United States Patent [19]

Talley et al.

[11] Patent Number: 5,633,272

[45] Date of Patent: May 27, 1997

[54] SUBSTITUTED ISOXAZOLES FOR THE TREATMENT OF INFLAMMATION

[76] Inventors: John J. Talley, 8772 Pine Ave., Brentwood, Mo. 63144; David L. Brown, 15504 Twingate, Chesterfield, Mo. 63017; Srinivasan Nagarajan, 16209 Forest Meadows Dr., Chesterfield, Mo. 63017; Jeffery S. Carter, 15321 Grantley Dr., Chesterfield, Mo. 63017; Richard M. Weier, 240 Hickory Ct., Lake Bluff, Ill. 60044; Michael A. Stealey, 502 Juniper Pkwy., Libertyville, Ill. 60048; Paul W. Collins, 1557 Hawthorne Pl., Deerfield, Ill. 60015; Roland S. Rogers, deceased, late of Richmond Heights, Mo. 63117, by Kathy L. Rogers, legal representative; Karen Seibert, 11930 Greenwalk Dr., St. Louis, Mo. 63146

[21] Appl. No.: 473,884

[22] Filed: Jun. 7, 1995

Related U.S. Application Data

[63] Continuation-in-part of Ser. No. 387,680, Feb. 13, 1995, abandoned.

[51] Int. Cl.$^6$ .................. C07D 261/06; C07D 261/10; C07D 261/12; C07D 261/14; A61K 31/42
[52] U.S. Cl. .................. 514/378; 548/182; 548/186; 548/190; 548/193; 548/202; 548/203; 548/225; 548/228; 548/229; 548/232; 548/234; 548/235; 548/243; 548/245; 548/247; 548/248; 546/272.1; 544/405; 514/255; 514/340; 514/365; 514/369; 514/370; 514/374; 514/376; 514/377; 514/380
[58] Field of Search .................. 548/247, 243, 548/245, 248; 514/380, 378

[56] References Cited

U.S. PATENT DOCUMENTS

| | | | |
|---|---|---|---|
| 5,310,926 | 5/1994 | Hagiwara et al. | 548/247 |
| 5,318,970 | 6/1994 | Suzuki et al. | 514/252 |

FOREIGN PATENT DOCUMENTS

| | | |
|---|---|---|
| 93/35480 | 10/1993 | Australia . |
| 026928 | 4/1981 | European Pat. Off. . |
| 549797 | 7/1993 | European Pat. Off. . |
| 623603 | 11/1994 | European Pat. Off. . |
| 633254 | 1/1995 | European Pat. Off. . |
| 4314966 | 11/1994 | Germany . |
| 2-223568 | 9/1990 | Japan . |
| 4-173780 | 6/1992 | Japan . |
| 92/19604 | 11/1992 | WIPO . |
| 94/17059 | 8/1994 | WIPO . |
| 94/20475 | 9/1994 | WIPO . |
| 95/00501 | 1/1995 | WIPO . |
| 95/12587 | 5/1995 | WIPO . |
| 95/14672 | 6/1995 | WIPO . |

OTHER PUBLICATIONS

Ichiro Yamawaki et al, Chem. Pharm. Bull., 36:3142–3146 @(1988).
Umezawa et al, Bull. Chem. Soc. Jpn vol. 36, No. 9, pp. 1150–1154 Sep. (1963).
Descamps et al, Bull. Soc. Chim. Belg., 73:459–82 (1964).
Hagiwara et al. CA 114:42776k, @1991.
Nagai et al., CA 117:212485w, @1992.

*Primary Examiner*—Johann Richter
*Assistant Examiner*—Laura L. Stockton
*Attorney, Agent, or Firm*—Joseph W. Bulock

[57] ABSTRACT

A class of substituted isoxazolyl compounds is described for use in treating inflammation and inflammation-related disorders. Compounds of particular interest are defined by Formula II

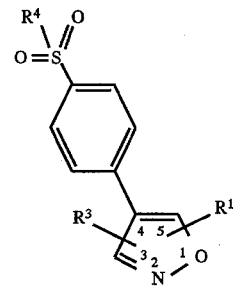

wherein $R^1$ is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxylalkyl, cycloalkyl, cycloalkylalkyl, and aralkyl; wherein $R^3$ is selected from cycloalkyl, cycloalkenyl, aryl, and heteroaryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, aminosulfonyl, and lower alkylthio; and wherein $R^4$ is selected from lower alkyl, hydroxyl and amino; or a pharmaceutically-acceptable salt thereof.

29 Claims, No Drawings

SUBSTITUTED ISOXAZOLES FOR THE TREATMENT OF INFLAMMATION

RELATED CASE

This application is a continuation-in part of U.S. patent application Ser. No. 08/387,680, filed Feb. 13, 1995 now abandoned.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel isoxazoles disclosed herein are such safe and also effective antiinflammatory agents furthering such efforts. The invention's compounds are found to show usefulness in vivo as antiinflammatory agents with minimal side effects. The substituted isoxazolyl compounds disclosed herein preferably selectively inhibit cyclooxygenase-2 over cyclooxygenase-1.

Isoxazoles have been described for various uses, including the treatment of inflammation. U.S. Pat. No. DE 4,314,966, published Nov. 10, 1994, describes 3-(2-hydroxyphenyl)isoxazoles for the treatment of inflammatory disorders. WO 92/05162, published Apr. 4, 1992, describes 5-piperazinyl-3,4-diaryl-isoxazoles as having medicinal use.

WO 92/19604, published Nov. 12, 1992, describes 5-alkene-3,4-diaryl-isoxazoles as having cyclooxygenase inhibition activity. EP 26928, published Apr. 15, 1981, describes 3,4-diaryl-isoxazole-5-acetic acids as having anti-inflammatory activity. WO 95/00501, published Jan. 5, 1995, generically describes 3,4-diaryl-isoxazoles as cyclooxygenase inhibitors.

The invention's isoxazolyl compounds are found to show usefulness in vivo as antiinflammatory agents with minimal side effects.

DESCRIPTION OF THE INVENTION

A class of substituted isoxazolyl compounds useful in treating inflammation-related disorders is defined by Formula I:

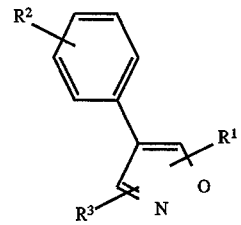

wherein $R^1$ is selected from hydroxyl, amino, alkyl, carboxyalkyl, alkoxycarbonyl, aminocarbonyl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocyclo, heterocycloalkyl, aryl, aralkyl, halo, alkylamino, aralkylamino, N-alkyl-N-aralkylamino, heteroaralkylamino, N-alkyl-N-heteroaralkylamino, N-alkyl-N-cycloalkylalkylamino, arylcarbonylthio, alkylaminocarbonylthioalkyl, arylcarbonyloxyalkyl, alkoxycarbonyloxyalkyl, alkylaminocarbonyloxyalkyl, alkoxycarbonylthioalkyl, and alkylaminocarbonylthioalkyl;

wherein $R^2$ is one or more radicals independently selected from alkyl, cyano, carboxyl, alkoxycarbonyl, haloalkyl, hydroxyl, hydroxyalkyl, haloalkoxy, amino, aminoalkyl, alkylamino, arylamino, nitro, alkoxyalkyl, alkylsulfinyl, halo, hydroxysulfonyl, alkylsulfonyl, aminosulfonyl, haloalkylsulfonyl, alkoxy and alkylthio;

wherein $R^3$ is selected from cycloalkyl, cycloalkenyl, aryl and heterocyclo; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, aminoalkyl, alkylamino, arylamino, nitro, alkoxyalkyl, alkylsulfinyl, aminosulfonyl, halo, alkoxy and alkylthio;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects. Besides being useful for human treatment, these compounds are also useful for treatment of mammals, including horses, dogs, cats, rats, mice, sheep, pigs, etc.

The present compounds may also be used in co-therapies, partially or completely, in place of other conventional antiinflammatories, such as together with steroids, NSAIDs, 5-lipoxygenase inhibitors, $LTB_4$ antagonists and $LTA_4$ hydrolase inhibitors.

Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the LTB4 inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present invention preferably includes compounds which selectively inhibit cyclooxygenase-2 over cyclooxygenase-1. Preferably, the compounds have a cyclooxygenase-2 $IC_{50}$ of less than about 0.5 µM, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 µM, and more preferably of greater than 20 µM. Such preferred selectivity may indicate an ability to reduce the incidence of common NSAID-induced side effects.

Within Formula I there is a subclass of compounds of high interest represented by Formula II:

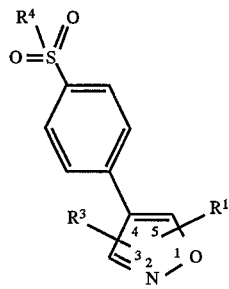

wherein $R^1$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino, N-alkyl-N-heteroaralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl;

wherein $R^3$ is selected from cycloalkyl, cycloalkenyl, aryl and heterocyclo; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and wherein $R^4$ is selected from alkyl, hydroxyl, and amino; or a pharmaceutically-acceptable salt thereof.

A preferred class of compounds consists of those compounds of Formula II wherein $R^1$ is selected from hydroxyl, amino, lower alkyl, lower carboxyalkyl, lower alkoxycarbonyl, aminocarbonyl, carboxyl, lower aminocarbonylalkyl, lower alkoxycarbonylalkyl, lower alkoxy, lower haloalkoxy, lower aralkoxy, lower heteroaralkoxy, lower cycloalkylalkoxy, lower alkylthio, lower aralkylthio, lower heteroaralkylthio, lower cycloalkylalkylthio, lower alkoxyalkyl, lower aralkoxyalkyl, lower alkylthioalkyl, lower aralkylthioalkyl, lower alkylaminoalkyl, lower aryloxyalkyl, lower arylthioalkyl, lower hydroxyalkyl, lower haloalkyl, lower cycloalkyl, lower cycloalkylalkyl, 5- or 6-membered heterocyclo, lower heterocycloalkyl, lower aralkyl, halo, lower alkylamino, lower aralkylamino, lower N-alkyl-N-aralkylamino, lower heteroaralkylamino, lower N-alkyl-N-heteroaralkylamino, lower N-alkyl-N-cycloalkylalkylamino, lower arylcarbonyloxyalkyl, lower alkoxycarbonyloxyalkyl, lower alkylaminocarbonyloxyalkyl, lower alkoxycarbonylthioalkyl, and lower alkylaminocarbonylthioalkyl; wherein $R^3$ is selected from cycloalkyl, cycloalkenyl, aryl, and heteroaryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, lower alkylsulfonyl, aminosulfonyl, and lower alkylthio; and wherein $R^4$ is selected from lower alkyl, hydroxyl and amino; or a pharmaceutically-acceptable salt thereof.

A more preferred class of compounds consists of those compounds of Formula II wherein $R^1$ is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxyalkyl, cycloalkyl, cycloalkylalkyl, and aralkyl; wherein $R^3$ is selected from cycloalkyl, cycloalkenyl, aryl, and heteroaryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, aminosulfonyl, and lower alkylthio; and wherein $R^4$ is selected from lower alkyl, hydroxyl and amino; or a pharmaceutically-acceptable salt thereof.

A class of compounds of particular interest consists of those compounds of Formula II wherein $R^1$ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzoxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected form benzyl and phenylethyl, wherein the phenyl ring is optionally substituted at a substitutable position with fluoro, chloro, bromo, iodo, methyl, and methoxy; wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, pyridyl, thienyl, thiazolyl, oxazolyl, furyl and pyrazinyl; wherein $R^3$ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, nitro, fluoro, chloro, bromo, iodo, methoxy, ethoxy, propoxy, n-butoxy, pentoxy, hexyloxy, methylenedioxy, aminosulfonyl, methylthio, ethylthio, butylthio, and hexylthio; and wherein $R^4$ is selected from methyl, hydroxyl and amino; or a pharmaceutically-acceptable salt thereof.

Within Formula I there is a subclass of compounds of high interest represented by Formula III:

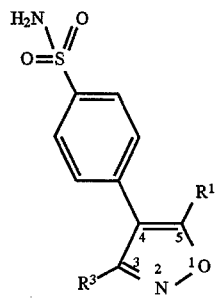

wherein $R^1$ is selected from hydroxyl, alkyl, carboxyalkyl, aminocarbonylalkyl, alkoxycarbonylalkyl, carboxyl, alkoxy, haloalkoxy, aralkoxy, heteroaralkoxy, cycloalkylalkoxy, alkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino, N-alkyl-N-heteroaralkylamino, alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl; and wherein $R^3$ is selected from cycloalkyl, cycloalkenyl, aryl and heterocyclo; wherein $R^3$ is optionally substituted at a substitutable position with one or more radicals independently selected from alkyl, cyano, carboxyl, alkoxycarbonyl, haloalkyl, hydroxyalkyl, haloalkoxy, amino, alkylamino, arylamino, aminoalkyl, nitro, alkoxyalkyl, alkylsulfinyl, aminosulfonyl, halo, alkoxy and alkylthio; or a pharmaceutically-acceptable salt thereof.

A preferred class of compounds consists of those compounds of Formula III wherein $R^1$ is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxylalkyl, lower cycloalkyl, lower cycloalkylalkyl, and aralkyl; wherein $R^3$ is selected from cycloalkyl, cycloalkenyl, aryl, and heteroaryl; and wherein $R^3$ is optionally substituted at a substitutable position with one or more radicals independently selected from lower alkylsulfinyl, aminosulfonyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy and lower alkylthio; or a pharmaceutically-acceptable salt thereof.

A class of compounds of particular interest consists of those compounds of Formula III wherein $R^1$ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzoxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected from phenylethyl and benzyl optionally substituted at a substitutable position with fluoro, chloro, bromo, iodo, methyl, and methoxy; and wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, pyridyl, thienyl, thiazolyl, oxazolyl, furyl and pyrazinyl; wherein $R^3$ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, aminomethyl, nitro, fluoro, chloro, bromo, iodo, methoxy, ethoxy, propoxy, n-butoxy, pentoxy, hexyloxy, methylenedioxy, methylthio, aminosulfonyl, ethylthio, butylthio, and hexylthio; or a pharmaceutically-acceptable salt thereof.

A class of compounds of more particular interest consists of those compounds of Formula III wherein $R^1$ is selected from methyl, ethyl, propyl, isopropyl, butyl, tert-butyl, isobutyl, pentyl, neopentyl, hexyl, hydroxymethyl, hydroxypropyl, methoxymethyl, difluoromethyl, trifluoromethyl, chloromethyl, cyclohexyl, cyclohexylmethyl, 4-chlorobenzyl, 3-chlorobenzyl, 4-methylbenzyl, 4-methoxybenzyl, carboxyl, carboxypropyl, carboxymethyl, carboxyethyl, methoxycarbonylmethyl, and ethoxycarbonylethyl; wherein $R^3$ is phenyl; wherein $R^3$ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, aminosulfonyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, aminomethyl, nitro, fluoro, chloro, bromo, iodo, methoxy, ethoxy, propoxy, n-butoxy, pentoxy, hexyloxy, methylenedioxy, methylthio, ethylthio, butylthio, and hexylthio; or a pharmaceutically-acceptable salt thereof.

Within Formula I there is a subclass of compounds of high interest represented by Formula IV:

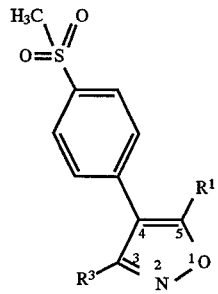

IV wherein $R^1$ is selected from alkyl and carboxyalkyl; and wherein $R^3$ is selected from cycloalkyl, cycloalkenyl, aryl and heterocyclo; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, aminosulfonyl, halo, alkoxy and alkylthio; or a pharmaceutically-acceptable salt thereof.

A family of specific compounds of particular interest within Formula I consists of compounds and pharmaceutically-acceptable salts thereof as follows:

[3-(3-fluoro-4-methoxyphenyl)-4-phenyl-isoxazol-5-yl] propanoic acid;
[3,4-diphenylisoxazol-5-yl]propanoic acid;
3-(3-fluoro-4-methoxyphenyl)-5-methyl-4-phenylisoxazole;
5-methyl-4-[4-(methylthio)phenyl]-3-phenylisoxazole;
3-(3-fluoro-4-methoxyphenyl)-5-methyl-4-[4-(methylthio) phenyl]isoxazole;
3-(3-chloro-4-methoxyphenyl)-5-methyl-4-[4-(methylthio) phenyl]isoxazole;
[4-[4-(methylthio)phenyl]-3-phenylisoxazol-5-yl]acetic acid;
(3,4-diphenylisoxazol-5-yl)acetic acid;
[3-(3-fluoro-4-methoxyphenyl)-4-[4-(methylsulfonyl) phenyl]isoxazol-5-yl]acetic acid;
[3-(3-chloro-4-methoxyphenyl)-4-[4-(methylsulfonyl) phenyl]isoxazol-5-yl]acetic acid;
5-methyl-4-[4-(methylsulfonyl)phenyl]-3-phenyl-isoxazole;
3-(3-chloro-4-methoxyphenyl)-5-methyl-4-[4-(methylsulfonyl)phenyl]isoxazole;
3-(3-chloro-4-methoxyphenyl)-5-ethyl-4-[4-(methylsulfonyl)phenyl]isoxazole;
3-(3-fluoro-4-methoxyphenyl)-5-ethyl-4-[4-(methylsulfonyl)phenyl]isoxazole;
3-(3,4-dichlorophenyl)-5-methyl-4-[4-(methylsulfonyl) phenyl]isoxazole;
3-(3,4-difluorophenyl)-5-methyl-4-[4-(methylsulfonyl) phenyl]isoxazole;
3-(3,5-difluoro-4-methoxyphenyl)-5-methyl-4-[4-(methylsulfonyl)phenyl]isoxazole;
3-(4-methoxyphenyl)-5-methyl-4-[4-(methylsulfonyl) phenyl]isoxazole;
3-(4-chlorophenyl)-5-methyl-4-[4-(methylsulfonyl)phenyl] isoxazole;
3-(4-fluorophenyl)-5-methyl-4-[4-(methylsulfonyl)phenyl] isoxazole;
3-(4-methylphenyl)-5-methyl-4-[4-(methylsulfonyl)phenyl] isoxazole;
4-[5-ethyl-3-phenylisoxazol-4-yl]benzenesulfonamide;
4-[5propyl-3-phenylisoxazol-4-yl]benzenesulfonamide;
4-[5-isopropyl-3-phenylisoxazol-4-yl]benzenesulfonamide;
4-[5-butyl-3-phenylisoxazol-4-yl]benzenesulfonamide;
4-[5-isobutyl-3-phenylisoxazol-4-yl]benzenesulfonamide;
4-[5-cyclohexyl-3-phenylisoxazol-4-yl] benzenesulfonamide;
4-[5-neopentyl-3-phenylisoxazol-4-yl]benzenesulfonamide;
4-[5-cyclohexylmethyl-3-phenylisoxazol-4-yl] benzenesulfonamide;
4-[5-(4-chlorophenyl)methyl-3-phenylisoxazol-4-yl] benzenesulfonamide;
4-[5-trifluoromethyl-3-phenylisoxazol-4-yl] benzenesulfonamide;
4-[5-difluoromethyl-3-phenylisoxazol-4-yl] benzenesulfonamide;
4-[5-chloromethyl-3-phenylisoxazol-4-yl] benzenesulfonamide;
4-[5-methyl-3-phenylisoxazol-4-yl]benzenesulfonic acid;
4-[5-propyl-3-phenylisoxazol-4-yl]benzenesulfonic acid;
4-[5-methoxymethyl-3-phenylisoxazol-4-yl] benzenesulfonamide;
4-[5-(3-hydroxypropyl)-3-phenylisoxazol-4-yl] benzenesulfonamide;
4-[3-(4-chlorophenyl)-5-methyl-isoxazol-4-yl] benzenesulfonamide;
4-[3-(4-fluorophenyl)-5-methyl-isoxazol-4-yl] benzenesulfonamide;
4-[3-(3-fluoro-4-methylphenyl)-5-methyl-isoxazol-4-yl] benzenesulfonamide;
4-[3-(3-aminosulfonyl-4-methoxyphenyl)-5-methyl-isoxazol-4-yl]benzenesulfonamide;
4-[3-(3-chloro-4-methylphenyl)-5-methyl-isoxazol-4-yl] benzenesulfonamide;
4-[5-methyl-3-(3-pyridyl)isoxazol-4-yl] benzenesulfonamide;
4-[5-methyl-3-(4-pyridyl)-isoxazol-4-yl] benzenesulfonamide;
4-[3-(3-fluorophenyl)-5-methyl-isoxazol-4-yl] benzenesulfonamide;
4-[5-hydroxymethyl-3-phenylisoxazol-4-yl] benzenesulfonamide;
[4-[4-(aminosulfonyl)phenyl]-3-phenylisoxazol-5-yl] carboxylic acid;
4-[5-hydroxy-3-phenyl-4-isoxazolyl]benzenesulfonamide;

4-[3-methyl-5-phenyl-isoxazol-4-yl]benzenesulfonamide;
4-[5-methyl-3-phenyl-isoxazol-4-yl]benzenesulfonamide;
4-[3-(3-fluoro-4-methoxyphenyl)-5-methyl-isoxazol-4-yl]benzenesulfonamide;
4-[3-(4-methoxyphenyl)-5-methyl-isoxazol-4-yl]benzenesulfonamide;
4-[3-(3,5-difluoro-4-methoxyphenyl)-5-methyl-isoxazol-4-yl]benzenesulfonamide;
4-[3-(3-chloro-4-methoxyphenyl)-5-methyl-isoxazol-4-yl]benzenesulfonamide;
4-[3-(3,5-dichloro-4-methoxyphenyl)-5-methyl-isoxazol-4-yl]benzenesulfonamide;
4-[3-(4-methylphenyl)-5-methyl-isoxazol-4-yl]benzenesulfonamide;
4-[5-methyl-3-(4-trifluoromethoxyphenyl)-isoxazol-4-yl]benzenesulfonamide;
4-[5-methyl-3-(4-trifluoromethylphenyl)-isoxazol-4-yl]benzenesulfonamide;
4-[3-(4-cyanophenyl)-5-methyl-isoxazol-4-yl]benzenesulfonamide;
4-[3-(4-methylsulfinylphenyl)-5-methyl-isoxazol-4-yl]benzenesulfonamide;
4-[3-(4-methylthiophenyl)-5-methyl-isoxazol-4-yl]benzenesulfonamide;
4-[3-(4-hydroxymethylphenyl)-5-methyl-isoxazol-4-yl]benzenesulfonamide;
4-[5-ethyl-3-(3-fluoro-4-methoxyphenyl)isoxazol-4-yl]benzenesulfonamide;
4-[5-benzyl-3-(3-fluoro-4-methoxyphenyl)isoxazol-4-yl]benzenesulfonamide;
4-[3-(3-fluoro-4-methoxyphenyl)-5-methoxy-isoxazol-4-yl]benzenesulfonamide;
4-[3-(3-fluoro-4-methoxyphenyl)-5-phenoxymethyl-isoxazol-4-yl]benzenesulfonamide;
4-[5-benzyloxymethyl-3-(3-fluoro-4-methoxyphenyl)-isoxazol-4-yl]benzenesulfonamide;
4-[3-(3-fluoro-4-methoxyphenyl)-5-methoxymethyl-isoxazol-4-yl]benzenesulfonamide;
4-[3-(3-fluoro-4-methoxyphenyl)-5-methylthiomethyl-isoxazol-4-yl]benzenesulfonamide;
4-[3-(3-fluoro-4-methoxyphenyl)-5-(3-thienyl) methylthio-isoxazol-4-yl]benzenesulfonamide;
4-[3-(3-fluoro-4-methoxyphenyl)-5-methoxycarbonylmethyl-isoxazol-4-yl]benzenesulfonamide;
4-[5-(aminocarbonylmethyl)-3-(3-fluoro-4-methoxyphenyl)-isoxazol-4-yl]benzenesulfonamide;
4-[3-(3-fluoro-4-methoxyphenyl)-5-methylthio-isoxazol-4-yl]benzenesulfonamide;
4-[3-(3-fluoro-4-methoxyphenyl)-5-(trifluoromethoxy)isoxazol-4-yl]benzenesulfonamide;
4-[3-(3-fluoro-4-methoxyphenyl)-5-(N-methylamino)isoxazol-4-yl]benzenesulfonamide;
[4-[4-(aminosulfonyl)phenyl]-3-phenyl-isoxazol-5-yl]acetic acid;
[4-[4-(aminosulfonyl)phenyl]-3-phenyl-isoxazol-5-yl]carboxamide;
methyl [4-[4-(aminosulfonyl)phenyl]-3-phenyl-isoxazol-5-yl]acetate;
[4-[4-(aminosulfonyl)phenyl]-3-phenyl-isoxazol-5-yl]propanoic acid;
ethyl [4-[4-(aminosulfonyl)phenyl]-3-phenyl-isoxazol-5-yl]propanoate; and
[4-[4-(aminosulfonyl)phenyl]-3-(3-fluoro-4-methoxyphenyl)isoxazol-5-yl]propanoic acid.

A second family of specific compounds of particular interest within Formula I consists of compounds and pharmaceutically-acceptable salts thereof as follows:

4-[5-ethyl-3-phenylisoxazol-4-yl]benzenesulfonamide;
4-[5-propyl-3-phenylisoxazol-4-yl]benzenesulfonamide;
4-[5-isopropyl-3-phenylisoxazol-4-yl]benzenesulfonamide;
4-[5-butyl-3-phenylisoxazol-4-yl]benzenesulfonamide;
4-[5-isobutyl-3-phenylisoxazol-4-yl]benzenesulfonamide;
4-[5-cyclohexyl-3-phenylisoxazol-4-yl]benzenesulfonamide;
4-[5-neopentyl-3-phenylisoxazol-4-yl]benzenesulfonamide;
4-[5-cyclohexylmethyl-3-phenylisoxazol-4-yl]benzenesulfonamide;
4-[5-(4-chlorophenyl)methyl-3-phenylisoxazol-4-yl]benzenesulfonamide;
4-[5-trifluoromethyl-3-phenylisoxazol-4-yl]benzenesulfonamide;
4-[5-difluoromethyl-3-phenylisoxazol-4-yl]benzenesulfonamide;
4-[5-chloromethyl-3-phenylisoxazol-4-yl]benzenesulfonamide;
4-[5-methyl-3-phenylisoxazol-4-yl]benzenesulfonic acid;
4-[5-propyl-3-phenylisoxazol-4-yl]benzenesulfonic acid;
4-[5-methoxymethyl-3-phenylisoxazol-4-yl]benzenesulfonamide;
4-[5-(3-hydroxypropyl)-3-phenylisoxazol-4-yl]benzenesulfonamide;
4-[3-(4-chlorophenyl)-5-methyl-isoxazol-4-yl]benzenesulfonamide;
4-[3-(4-fluorophenyl)-5-methyl-isoxazol-4-yl]benzenesulfonamide;
4-[3-(3-fluoro-4-methylphenyl)-5-methyl-isoxazol-4-yl]benzenesulfonamide;
4-[3-(3-aminosulfonyl-4-methoxyphenyl)-5-methyl-isoxazol-4-yl]benzenesulfonamide;
4-[3-(3-chloro-4-methylphenyl)-5-methyl-isoxazol-4-yl]benzenesulfonamide;
4-[5-methyl-3-(3-pyridyl)isoxazol-4-yl]benzenesulfonamide;
4-[5-methyl-3-(4-pyridyl)-isoxazol-4-yl]benzenesulfonamide;
4-[3-(3-fluorophenyl)-5-methyl-isoxazol-4-yl]benzenesulfonamide;
4-[5-hydroxymethyl-3-phenylisoxazol-4-yl]benzenesulfonamide;
[4-[4-(aminosulfonyl)phenyl]-3-phenylisoxazol-5-yl]carboxylic acid;
4-[5-hydroxy-3-phenyl-4-isoxazolyl]benzenesulfonamide;
4-[3-methyl-5-phenyl-isoxazol-4-yl]benzenesulfonamide;
4-[5-methyl-3-phenyl-isoxazol-4-yl]benzenesulfonamide;
4-[3-(3-fluoro-4-methoxyphenyl)-5-methyl-isoxazol-4-yl]benzenesulfonamide;
[3-(3-chloro-4-methoxyphenyl)-4-[4-(methylsulfonyl)phenyl]isoxazol-5-yl]acetic acid;
5-methyl-4-[4-(methylsulfonyl)phenyl]-3-phenyl-isoxazole;
3-(3-chloro-4-methoxyphenyl)-5-methyl -4-[4-(methylsulfonyl)phenyl]isoxazole;
[4-[4-(aminosulfonyl)phenyl]-3-phenyl-isoxazol-5-yl]acetic acid;
[4-[4-(aminosulfonyl)phenyl]-3-phenyl-isoxazol-5-yl]propanoic acid;
ethyl [4-[4-(aminosulfonyl)phenyl]-3-phenyl-isoxazol-5-yl]propanoate;
[4-[4-(aminosulfonyl)phenyl]-3-(3-fluoro-4-methoxyphenyl)isoxazol-5-yl]propanoic acid; and
[3-(3-fluoro-4-methoxyphenyl)-4-[4-(methylsulfonyl)phenyl]isoxazol-5-yl]acetic acid.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The terms "hydroxyalkyl" and "hydroxylalkyl" embrace linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cycloalkoxy" embraces radicals having cycloalkyl radicals, as defined above, attached to an alkoxy radical. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The terms "heterocyclic" and "heterocyclo" embrace saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3-to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclic group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclic group containing 1 to 2 sulfur atoms and 1 to 3 nitrogen atoms (e.g., benzothiazolyl, benzothiadiazolyl, etc.) and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "cycloalkylalkylthio" embraces radicals having cycloalkyl radicals, as defined above, attached to an alkylthio radical. More preferred cycloalkylthio radicals are "lower cycloalkylalkylthio" radicals having cycloalkyl radicals of three to six carbon atoms. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote $NH_2O_2S$—. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" means a radical containing an alkoxycarbonyl radical, as defined above, attached to an alkyl radical. Examples of such "alkoxycarbonylalkyl" ester radicals include substituted or unsubstituted methoxycarbonylmethyl, butoxycarbonylmethyl and hexyloxycarbonylethyl. The terms "alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include substituted or unsubstituted methylcarbonyl, ethylcarbonyl, phenylcarbonyl and benzylcarbonyl. The term "aralkyl" embraces arylsubstituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocycloalkyl" embraces heterocyclo-substituted alkyl radicals, such as pyrrolidinylmethyl, piperazinylmethyl, piperidinylmethyl, furanylethyl, tetrahydrofurylethyl and heteroaralkyl radicals. The term "heteroaralkyl" embraces heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "cycloalkylalkyl" embraces cycloalkyl-substituted alkyl radicals such as cyclohexylmethyl, cyclopentylethyl, cyclopentylmethyl, cyclohexylethyl, and cyclobutylpropyl. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "heteroaralkoxy" embraces heteroaralkyl radicals attached through an oxygen atom to other radicals. The term "heteroaralkylthio" embraces heteroaralkyl radicals attached through a sulfur atom to other radicals. The term "aminoalkyl" embraces alkyl radicals substituted with amino radicals. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "cycloalkylamino" denotes amino groups which have been substituted with one or two cycloalkyl radicals, as defined above. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The term "heteroaralkylamino" embraces heteroaralkyl radicals, as defined above, attached through an nitrogen atom to other radicals. The term "aminocarbonyl" denotes an amide group of the formula —C(=O)$NH_2$. The term "alkylcarbonylaminoalkyl" embraces radicals having one or more alkyl radicals attached to a carbonyl radical further attached to an aminoalkyl radical. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

The present invention comprises a pharmaceutical composition comprising a therapeutically-effective amount of a compound of Formulas I–IV in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formulas I–IV.

Also included in the family of compounds of Formulas I–IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I–IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formulas I–IV include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I–IV by reacting, for example, the appropriate acid or base with the compound of Formulas I–IV.

GENERAL SYNTHETIC PROCEDURES

The compounds of the invention can be synthesized according to the following procedures of Schemes I–XIII, wherein the $R^1$–$R^4$ substituents are as defined for Formulas I–IV, above, except where further noted.

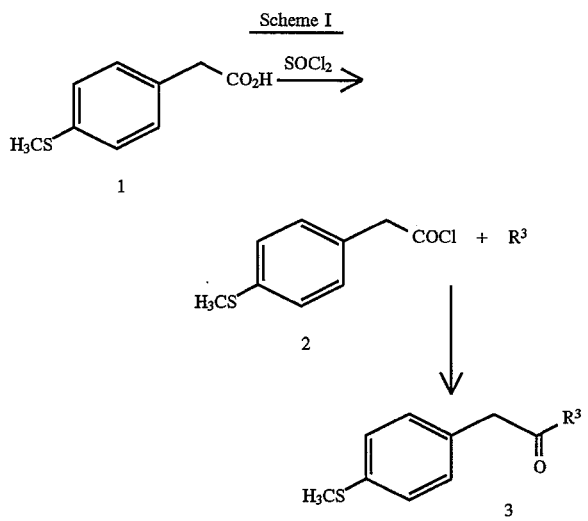

Scheme I illustrates the two step procedure used to prepare substituted desoxybenzoin derivatives 3. In step one, 4-methylthiophenylacetic acid 1 is converted to the corresponding acid chloride 2 with thionyl chloride. A variety of aromatic compounds are then acylated with 2 in the presence of a Lewis acid such as aluminum chloride to provide the desired desoxybenzoins 3 in high yield. This Friedel Crafts acylation can be performed in an inert solvent, such as dichloromethane, chloroform, nitrobenzene, 1,2-dichloroethane, 1,2-dichlorobenzene and similar solvents.

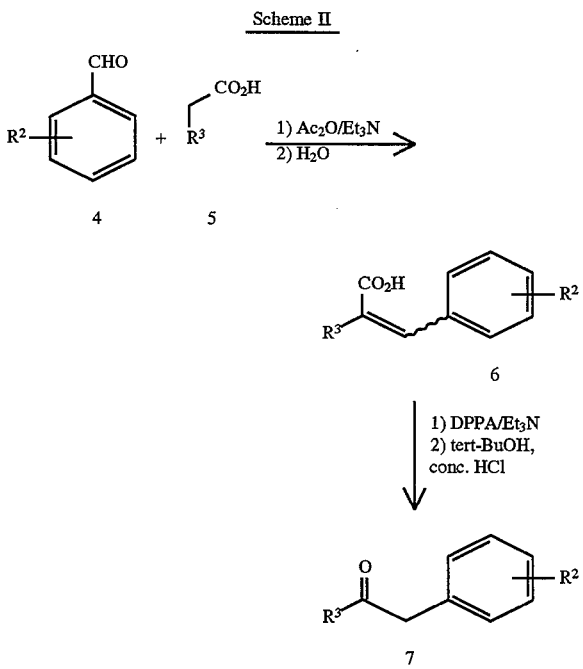

Synthetic Scheme II shows the four step procedure which can be used to prepare substituted ketone compounds 7 from aldehyde 4 and acid 5. In step one, aldehyde 4 and substituted acetic acid 5 are heated together in acetic anhydride and triethylamine to form the 2,3-disubstituted acrylic acids 6 via a Perkin condensation. In step two, the addition of water produces the acids 6 free from any mixed acetic-acrylic anhydrides. In step three, the acrylic acids 6 are reacted with diphenylphosphorylazide (DPPA) and triethylamine in toluene at about 0° C. and then at room temperature to form acylazides. In step four, the crude acylazides are heated to form a vinyl isocyanate via a Curtius rearrangement. The vinyl isocyanates are trapped with tert-butyl alcohol to produce N-tert-butoxycarbonyl enamine derivatives. Acidic hydrolysis using concentrated HCl provides the substituted ketone 7 intermediates.

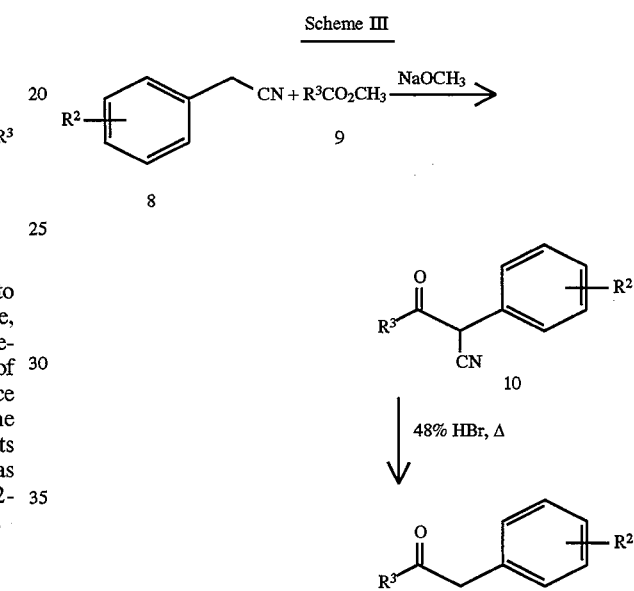

Synthetic Scheme III illustrates an alternative approach which can be used to prepare substituted ketone intermediates 7 via the Claisen reaction of a substituted phenylacetonitrile 8 and a acid ester 9. In the first step, a mixture of substituted phenylacetonitrile 8 and acid ester 9 are treated with a base such as sodium methoxide in a protic solvent like methanol to provide the cyanoketone 10. In step two, the cyanoketone 10 is hydrolyzed in aqueous acid such as concentrated HBr to effect hydrolysis of the nitrile and decarboxylation of the incipient carboxylic acid to produce the substituted ketone intermediates 7.

Other synthetic approaches are possible to form the desired ketones 7. These alternatives include reacting the appropriate Grignard or lithium reagents with Weinreb amides of substituted acids or acetic acids. The Weinreb methodology has been reported in *Tetrahedron Letters*, 4171 (1977).

Scheme IV

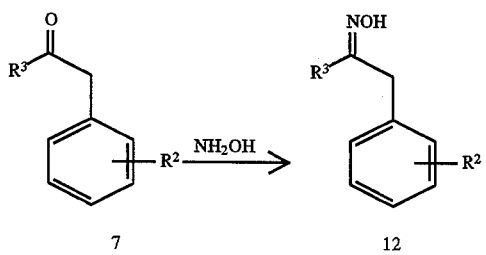

Synthetic Scheme IV shows the procedure which can be used for the preparation of oxime intermediates 12. Treatment of ketone intermediates 7 with hydroxylamine, generally prepared from hydroxylamine hydrochloride by potassium hydroxide, provides the oxime intermediates 12. A wide variety of solvents can be used for this reaction including ethanol, toluene and tetrahydrofuran.

Scheme V

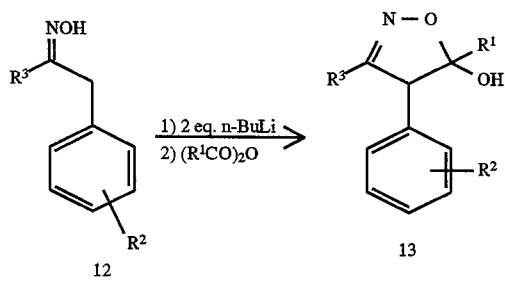

Synthetic Scheme V shows the procedure which can be used for the preparation of hydrated isoxazole derivatives 13. The substituted oximes 12 are treated with two equivalents of a base such as n-butyllithium in hexanes to produce a dianion which is subsequently acylated. Suitable acylating agents are anhydrides, acyl imidazoles, esters and the like. Upon quenching the reaction mixture with dilute aqueous acid, hydrated isoxazole derivatives 13 can be isolated by crystallization or chromatography.

Scheme VI

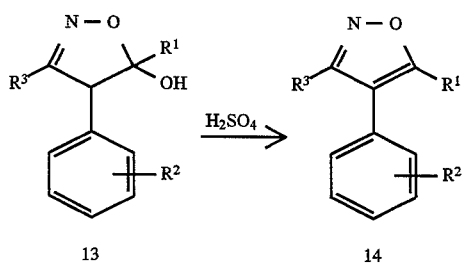

Synthetic Scheme VI shows the procedure which can be used for the preparation of isoxazole analogs 14 by dehydration of the hydrated isoxazole derivatives 13. Substituted hydrated isoxazoles 13 are dissolved in an appropriate solvent such as toluene and then treated with a catalytic to stoichiometric amount of concentrated sulfuric acid to effect dehydration and thereby produce isoxazole derivatives 14. Other acids can also be employed to effect this transformation such as concentrated HCl, concentrated HBr and many others.

Scheme VII

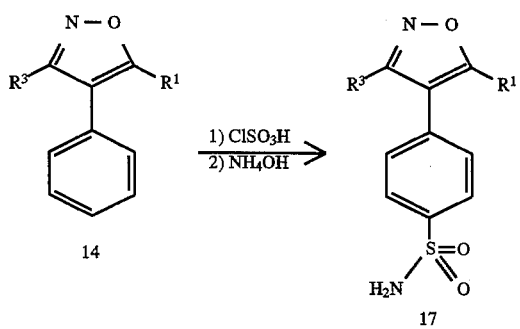

Synthetic Scheme VII shows the procedure which can be used for the preparation of substituted 4-[4-(methylsulfonyl)phenyl]isoxazole analogs 16 from the corresponding 4-[4-(methylthio)phenyl]isoxazoles 15. The oxidation of an aromatic methythio derivative 15 to the corresponding aromatic methylsulfonyl compound 16 can be accomplished in a variety of ways such as with two equivalents of meta-chloroperoxybenzoic acid (MCPBA), two equivalents of Oxone® (potassium peroxymonosulfate) and many other oxidizing agents.

Scheme VIII

Synthetic Scheme VIII shows the procedure which can be used for the preparation of substituted 4-(4-aminosulfonyl)phenylisoxazole analogs 17 from the corresponding 4-phenylisoxazoles 14. The procedure is a two step process for the direct introduction of the sulfonamide moiety into 4-phenylisoxazoles 14 or hydrated isoxazoles 13. In step one, isoxazole 14 or hydrated isoxazole 13 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 17.

Scheme IX

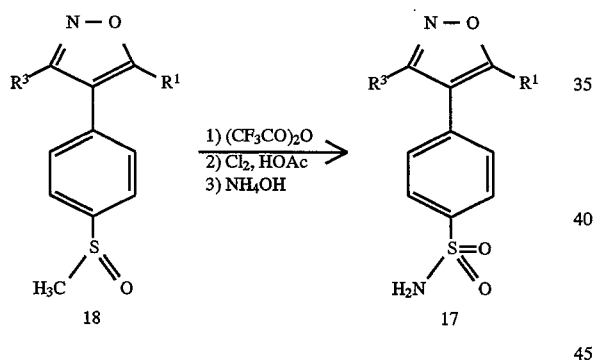

Synthetic Scheme IX shows the three step procedure used to prepare sulfonamide antiinflammatory agents 17 from their corresponding methyl sulfones 16. In step one, a tetrahydrofuran solution (THF) of the methyl sulfones 16 are treated with an alkyllithium or alkylmagnesium (Grignard) reagent at −78° C., such as n-propyl magnesium bromide. In step two, the anion generated in step one is treated with an organoborane, such as tri-n-butylborane at −78° C. then warmed to room temperature and then heated to reflux. In step three, an aqueous solution of hydroxylamine-o-sulfonic acid is added to provide the corresponding sulfonamide antiinflammatory agents 17. This procedure is essentially that of Huang et. al., *Tetrahedron Letters*, 35, 7204 (1994).

Scheme X

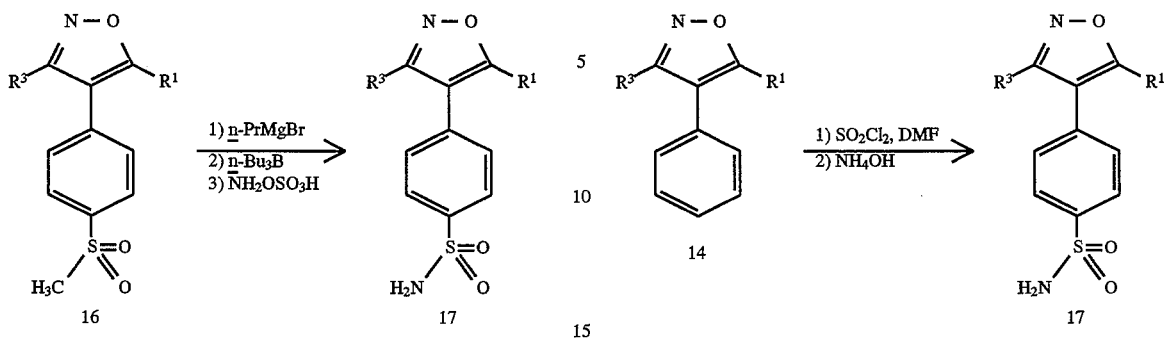

Synthetic Scheme X shows the three step procedure used to prepare sulfonamide antiinflammatory agents 17 from their corresponding methylsulfinyl analogs 18. Methylsulfinyl derivatives 18 are available from the corresponding methylthio compounds 15 by oxidation with one equivalent of an oxidizing agent such as MCPBA. In step one, the methylsulfinyl compounds 18 are treated with trifluoroacetic anhydride to effect Pummerer rearrangement. In step two, the crude Pummerer rearrangement product dissolved in acetic acid is treated with chlorine gas to produce a sulfonyl chloride. In step three, the sulfonyl chloride is converted to the corresponding sulfonamide antiinflammatory agents 17 by treatment with concentrated ammonia. This procedure was adapted from Kharash, *J. Am. Chem. Soc.*, 73, 3240 (1951).

Scheme XI

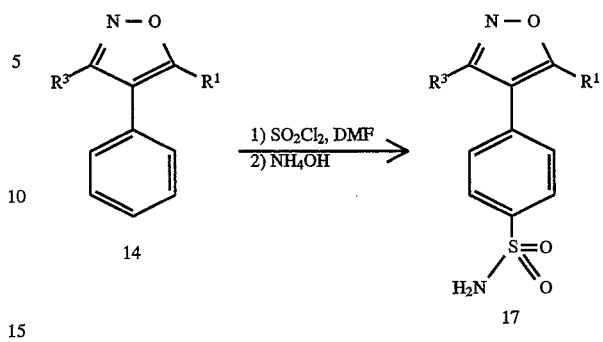

Synthetic Scheme XI shows the two step procedure used to prepare sulfonamide antiinflammatory agents 17 from their corresponding 4-phenyl isoxazole derivatives 14. In step one a mixture of sulfuryl chloride and dimethylformamide (DMF) are allowed to react at room temperature and then mixed with 4-phenylisoxazoles 14 and heated to about 100° C. The sulfonyl chloride thus formed is then treated with an excess of concentrated ammonia to provide the antiinflammatory sulfonamides 17.

Scheme XII

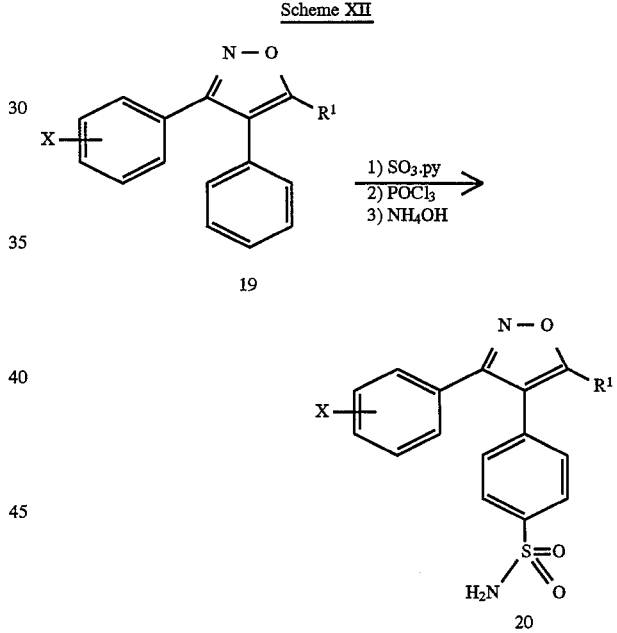

Synthetic Scheme XII shows the three step procedure used to prepare sulfonamide antiinflammatory agents 20 from 4-phenyl isoxazoles 19. In step one, the 4-phenylisoxazoles 19 are converted into the corresponding sulfonic acid by treatment with sulfur trioxide pyridine (pyridine) complex at about 100° C. In step two, the sulfonic acid is converted into the sulfonyl chloride by the action of phosphorus oxychloride and in step three the sulfonyl chloride is treated with excess concentrated ammonia to provide the antiinflammatory sulfonamides 20.

Scheme XIII

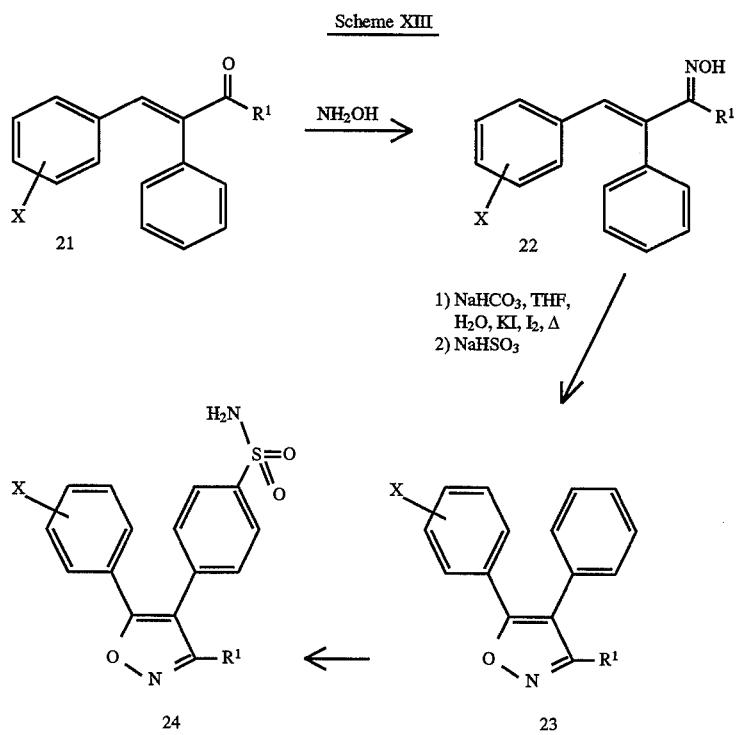

Synthetic Scheme XIII shows the three step procedure used to prepare 4,5-diphenylisoxazole antiinflammatory agents 24 from 1,2-diphenylbutenones 21. In step one, the 1,2-diphenylketones 21 are converted to the corresponding oximes 22 by treatment with hydroxylamine in a manner similar to that shown in Scheme IV. In step two, the oxime 22 is converted to the 4,5-diphenylisoxazole 23 in two steps. The oxime 22 is reacted with potassium iodide and iodine in the presence of base, such as sodium bicarbonate and heated to form the halo intermediate. Sodium bisulfite is added to form the isoxazole 23. The isoxazole 23 is converted to the sulfonamide by any of the procedures shown in Schemes VIII, XI or XII.

The following examples contain detailed descriptions of the methods of preparation of compounds of Formulas I–IV. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

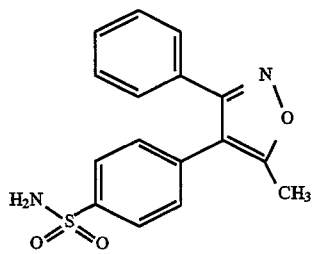

4-[5-Methyl-3-phenylisoxazol-4-yl]benzenesulfonamide

Step 1. Preparation of desoxybenzoin keto-oxime.

Desoxybenzoin (20.0 g, 0.102 mol) was dissolved in toluene (200 mL). In a separate 500 mL round-bottom flask equipped with a magnetic stirring bar, hydroxylamine hydrochloride (9.21 g, 0.132 mol) and potassium hydroxide (7.43 g, 0.132 mol) were suspended in absolute ethanol (50 mL) and stirred vigorously at room temperature for thirty minutes. The desoxybenzoin solution was added in one portion, and the yellow suspension was held at reflux, using a Dean-Stark trap to remove generated water, under a nitrogen blanket for 16 hours. The suspension was cooled to room temperature and poured into water (200 mL). The system was extracted with ethyl acetate (2×150 mL), then the combined organic solution was washed with brine (200 mL), dried over magnesium sulfate, and filtered. The solvents were evaporated under reduced pressure to yield a crude solid. The solid was recrystallized from hot ethanol/water, filtered and washed with water to yield, upon drying, desoxybenzoin keto-oxime as white crystals (17.7 g, 82%): mp 87°–90° C. Mass spectrum, MH+=212. High resolution mass spectrum Calc'd. for $C_{14}H_{13}NO$: 211.0997. Found: 211.0949.

Step 2. Preparation of 4-[5-methyl-3-phenylisoxazol-4-yl]benzensulfonamide.

A solution of desoxybenzoin keto-oxime from Step 1 (6.00 g; 28.40 mmol) in anhydrous tetrahydrofuran (THF, 80 mL) was cooled to −20° C. in an oven-dried 250 mL three-neck round-bottom flask equipped with a thermometer, nitrogen gas inlet, rubber septum and provisions for magnetic stirring. To this cold solution, n-butyllithium (1.6N in hexanes, 44.4 mL) was added, via syringe, over 35 minutes, such that the reaction temperature remained at or below −10° C. The deep red solution was stirred at −10° C. for 1 hour, warmed to room temperature, then stirred at room temperature for an additional hour. Acetic anhydride (3.2 mL, 34.1 mmol) was added in one portion, and the resulting suspension was stirred without temperature control for 2 hours. Water (100 mL) was added, and the solution was poured into 1N HCl (100 mL) and extracted with ethyl acetate (2×200 mL). The combined organic solution was washed with hydrochloric acid (1N HCl, 100 mL) and brine (100 mL), dried over magnesium sulfate and filtered. The resulting solution was evaporated under reduced pressure to yield a crude oil. The oil was applied to a column of silica gel and eluted with ethyl acetate/hexane (10–50% ethyl acetate) to yield, upon concentration of the appropriate fractions, 5.0 g of 3,4-diphenyl-4-hydrido-5-hydroxy-5-methylisoxazole. The solid was cooled to 0° C., then dissolved in cold chlorosulfonic acid (15 mL). The brown solution was stirred at 0° C. for 2 hours, then added dropwise to a stirring suspension of ice (200 mL) and dichloromethane (200 mL). The layers were separated, and the organic phase was added directly to a saturated ammonium hydroxide solution (100 mL) at 0° C. This biphasic solution was vigorously stirred at 0° C. for 2 hours, the layers were separated, and the aqueous phase was washed with dichloromethane (50 mL). The combined organic solution was dried over magnesium sulfate, filtered and evaporated under reduced pressure to approximately one-half of its original volume. Crystals formed. The stirred suspension was cooled to 0° C. and held for 30 minutes. The crystals were filtered, washed with cold dichloromethane and dried to yield 4-[5-methyl-3-phenylisoxazol-4-yl]benzenesulfonamide (2.7 g, 30%): mp 155°–157° C. $^1$H NMR ($CD_3CN$/500 MHz) δ 7.86 (d, J=8.39 Hz, 2H), 7.45 (m, 1H), 7.39 (s, 4H , 7.37 (d, J=8.39 Hz, 2H), 5.70 (s, 2H), 2.46 (s, 3H Mass Spectrum, MH+=315.

Proceeding an a like manner but replacing the anhydrides with other appropriately substituted anhydrides and esters, the following compounds were prepared:

1a) 4-[5-ethyl-3-phenylisoxazol-4-yl]benzenesulfonamide: mp 140°–141° C. $^1$H NMR ($CDCl_3$) δ 7.93 (d, J=8.66, 2 H), 7.28–7.42 (m, 7 H), 4.81 (s, 2H), 2.83 (q, J=7.65 Hz, 2 H), 1.34 (t, J=7.45, 3 H). Mass spectrum M$^+$H 329. Anal. Calc'd. for $C_{17}H_{16}N_2O_3S$: C, 62.18; H, 4.91; N, 8.53; S, 9.76. Found: C, 62.07; H, 4.88; N, 8.42; S, 9.61.

1a) 4-[5-propyl-3-phenylisoxazol-4-yl]benzenesulfonamide: mp 147°–148° C. $^1$H NMR ($CDCl_3$) δ 7.92 (d, J=8.46, 2 H), 7.28–7.44 (m, 7 H), 4.83 (s, 2 H), 2.77 (t, J=7.25, 2 H), 1.71–1.85 (m, 2H), 0.98 (t, J=7.45, 3 H). Anal. Calc'd. for $C_{18}H_{18}N_2O_3S_1$: C, 63.14; H, 5.30; N, 8.18; S, 9.36. Found: C, 63.19; H, 5.32; N, 8.23; S, 9.44. Mass spectrum M$^+$H 343.

1c) 4-[5-isopropyl-3-phenylisoxazol-4-yl]benzenesulfonamide: mp 166°–168° C. $^1$H NMR ($CDCl_3$) δ 7.93 (d, J=8.46 Hz, 2 H), 7.27–7.40 (m, 7H), 4.80 (s, 2 H), 3.08–3.20 (m, 1 H), 1.36 (d, J=6.58 Hz, 6 H). Mass spectrum M$^+$H 343.

1d) 4-[5-butyl-3-phenylisoxazol-4-yl]benzenesulfonamide: mp 129°–131° C. $^1$H NMR ($CDCl_3$) δ 7.93 (d, J=8.46 Hz, 2H), 7.30–7.40 (m, 7H), 4.81 (s, 2H), 2.79 (t, J=7.45, 2H), 1.67–1.79 (m, 2H), 1.30–1.42 (m, 2H), 0.91 (t, J=7.25, 3 H). Anal. Calc'd. for $C_{19}H_{20}N_2O_3S_1$: C, 64.02; H, 5.66; N, 7.86; S, 8.99. Found: C, 63.22; H, 5.52; N, 7.51; S, 8.67.

1e) 4-[5-isobutyl-3-phenylisoxazol-4-yl]benzenesulfonamide: mp 159°–160° C. $^1$H NMR ($CDCl_3$) δ 7.93 (d, J=8.46, 2 H), 7.28–7.42 (m, 7H), 4.84 (s, 2H), 2.66 (d, J=7.25 Hz, 2H), 2.08–2.22 (m, 1 H), 0.94 (d, J=6.65 Hz, 6 H). High resolution mass spectrum Calc'd. for $C_{19}H_{20}N_2O_3S$: 221.0841. Found: 221.0827. Anal. Calc'd. for $C_{19}H_{20}N_2O_3S_1$: C, 64.02; H, 5.66; N, 7.86; S, 8.99. Found: C, 63.94; H, 5.65; N, 7.86; S, 8.90.

1f) 4-[5-cyclohexyl-3-phenylisoxazol-4-yl]benzenesulfonamide: mp 191°–193° C. $^1$H NMR ($CDCl_3$) δ 7.94 (d, J=8.46 Hz, 2 H), 7.27–7.41 (m, 7H), 4.85 (s, 2H), 2.62–2.85 (m, 1H), 1.67–1.95 (m, 7 H), 1.22–1.38 (m, 3 H). Mass spectrum M$^+$H 383. High resolution mass spectrum Calc'd. for $C_{21}H_{22}N_2O_3S$: 383.1429. Found: 383.1452.

1g) 4-[5-neopentyl-3-phenylisoxazol-4-yl]benzenesulfonamide: $^1$H NMR ($CDCl_3$) δ 7.94 (d, J=8.46, 2 H), 7.26–7.39 (m, 7 H), 4.82 (s, 2 H), 2.71 (s, 2 H), 0.94 (s, 9H). Mass spectrum M$^+$H 371.

1h) 4-[5-cyclohexylmethyl-3-phenylisoxazol-4-yl]benzenesulfonamide: mp 151°–153° C. $^1$H NMR ($CDCl_3$) δ 7.93 (d, J=8.46 Hz, 2 H), 7.29–7.43 (m, 7H), 4.82 (s, 2H), 2.67 (d, J=7.05 Hz, 2 H), 1.60–1.92 (m, 5 H), 0.85–1.30 (m, 6 H). Mass spectrum M$^+$H 397.

1i) 4-[5-(4-chlorophenyl)methyl-3-phenylisoxazol-4-yl]benzenesulfonamide: mp 107°–108° C. $^1$H NMR ($CDCl_3$ and $CD_3OD$) δ 7.91 (d, J=8.46, 2 H), 7.26–7.42 (m, 9H), 7.14 (d, J=8.46 Hz, 2 H), 4.85 (s, 2 H), 4.10 (s, 2 H). Mass spectrum M$^+$H=425. High resolution mass spectrum Calc'd. for $C_{22}H_{17}ClN_2O_3S$: 425.0727. Found: 425.0736.

1j) 4-[5-trifluoromethyl-3-phenylisoxazol-4-yl]benzenesulfonamide.

1k) 4-[5-difluoromethyl-3-phenylisoxazol-4-yl]benzenesulfonamide: mp 172°–175° C. $^1$H NMR ($CDCl_3$) δ 7.97 (d, J=8.46, 2 H), 7.30–7.50 (m, 7H), 6.72 (t, J=52.57 Hz, 1 H) , 4.87 (s, 2H). $^{19}$F NMR ($CHCl_3$) −116.45 (d, J=53.02 Hz). Mass spectrum M$^+$H 351.

1l) 4-[5-chloromethyl-3-phenylisoxazol-4-yl]benzenesulfonamide: mp 131°–133° C. $^1$H NMR ($CDCl_3$) d 7.98 (d, J=8.46, 2 H), 7.34–7.46 (m, 7H), 4.84 (s, 2H), 4.61 (s, 2 H). Mass spectrum M$^+$H 349. High resolution mass spectrum for $C_{16}H_{13}ClN_2O_3S$: 348.0335. Found: 348.0316.

1m) 4-[5-methyl-3-phenylisoxazol-4-yl]benzenesulfonic acid: mp 260°–269° C. $^1$H NMR ($CD_3OD$) δ 9.03 (s, >1 H exch), 8.42 (d, J=8.06 Hz, 2H), 8.12–8.28 (m, 5 H), 7.97 (d, J =8.26 Hz, 2 H). Mass spectrum M$^+$H 316.

1n) 4-[5-propyl-3-phenylisoxazol-4-yl]benzenesulfonic acid: $^1$H NMR ($CDCl_3$ and $CD_3OD$) δ 7.95–7.78 (m, 2 H), 7.10–7.40 (m, 7H), 2.65–2.78 (m, 2 H), 1.65–1.80 (m, 2H), 0.88–0.99 (m, 3H). Mass spectrum M$^+$H 344.

1o) 4-[5-methoxymethyl-3-phenylisoxazol-4-yl]benzenesulfonamide: mp 82°–118° C. $^1$H NMR (CDCl$_3$) δ 7.93 (d, J=8.66 Hz, 2 H), 7.31–7.45 (m, 7 H), 4.81 (s, 2 H), 4.51 (s, 2 H), 3.48 (s, 3 H). Mass spectrum M$^+$H 345. High resolution mass spectrum Calc'd. for $C_{17}H_{16}N_2O_4S$: 344.0831. Found: 344.0807.

1p) 4-[5-(3-hydroxypropyl)-3-phenylisoxazol-4-yl]benzenesulfonamide: mp 88°–142° C. $^1$H NMR (CDCl$_3$ and CD$_3$OD) δ 7.90 (d, J=8.66 Hz, 2 H), 7.26–7.42 (m, 7H), 3.66 (t, J=6.04 Hz, 2 H), 2.91 ( t, J=7.45 Hz, 2 H), 1.93–2.02 (m, 2H). Mass spectrum M$^+$H 349. High resolution mass spectrum Calc'd. for $C_{18}H_{18}N_2O_4S$: 358.0987. Found: 358.0958.

EXAMPLE 2

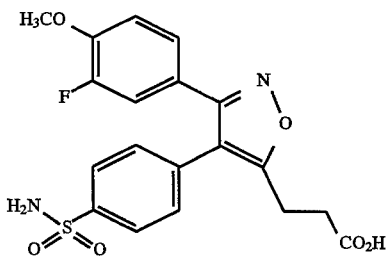

[4-[4-(Aminosulfonyl)phenyl]-3-(3-fluoro-4-methoxyphenyl)isoxazol-5-yl]propanoic Acid Step 1: Preparation of 1-(3-fluoro-4-methoxyphenyl)-2-phenyl-ethan-1-one.

In a 500 mL, 3-neck round-bottom flask, equipped with a pressure equalizing dropping funnel, thermometer, gas inlet tube and provisions for magnetic stirring, a suspension of aluminum chloride (9.4 g, 70.5 mmol) in a solution of 2-fluoroanisole (6.6 mL, 58.8 mmol) and anhydrous chloroform (200 mL) was cooled to 0° C. under a blanket of dry nitrogen. A solution of phenylacetyl chloride (8.6 mL, 64.7 mmol) in anhydrous chloroform (50 mL) was added to the vigorously stirred suspension over 20 minutes keeping the reaction temperature <5° C. The yellowish solution was stirred at 0° C. for 1 hour, then poured into ice (200 mL) and stirred without temperature control for 16 hours. The layers were separated, and the aqueous layer was extracted with dichloromethane (2×100 mL). The combined organic solution was dried over magnesium sulfate, filtered, and the solvent was evaporated under reduced pressure. The resulting solid was recrystallized from boiling hexane to yield, upon filtration and drying, 12.9 g (90%) of 1-(3-fluoro-4 methoxyphenyl)-2-phenyl-ethan-1-one as white crystals: $^1$H NMR (CDCl$_3$/300 MHz) δ 7.82–7.72 (m, 2H), 7.35–7.24 (m, 5H), 6.98 (dd, J=8.46, 8.26 Hz, 1H), 4.22 (s, 2H), 3.94 (s, 3H). $^{19}$F NMR (CDCl$_3$/282.2 MHz) −134.875 (m).

Step 2: Preparation of 1-(3-fluoro-4-methoxyphenyl)-2-phenyl-ethan-1-one oxime.

Hydroxylamine hydrochloride (3.7 g, 53.2 mmol) and potassium hydroxide (2.98 g, 53.2 mmol) were suspended in absolute ethanol (25 mL) and vigorously stirred in a 250-mL round-bottom flask equipped with a magnetic stirring bar under a dry nitrogen blanket for 30 minutes. To this, a suspension of 1-(3-fluoro-4-methoxyphenyl)-2-phenyl-ethan-1-one from Step 1 (10.0 g, 40.9 mmol) in toluene (150 mL) was added in one portion. A Dean-Stark trap and reflux condenser were added to the apparatus, and the yellow suspension was warmed to reflux. The solution was maintained at reflux 16 hours, then the suspension was cooled to room temperature. Water (100 mL) was added, and the resulting solution was extracted with ethyl acetate (2×100 mL). The combined organic solution was washed with brine (100 mL), dried over magnesium sulfate and filtered. The resulting solution was evaporated under reduced pressure to yield a crude residue. The residue was crystallized from boiling ethanol/water to yield, upon filtration and drying, 10.0 g (94%) of 1-(3-fluoro-4-methoxyphenyl)-2 phenyl-ethan-1-one oxime as ivory-colored crystals: $^1$H NMR (CDCl$_3$/300 MHz) δ 7.42 (dd, J=12.69, 2.01, 1H), 7.36–7.19 (m, 6H), 6.89 (dd, J=8.66, 8.46 HZ, 1H), 4.16 (s, 2H), 3.88 (s, 3H). $^{19}$F NMR (CDCl$_3$/282.2 MHz): 135.517 (m).

Step 3: [3-(3-fluoro-4-methoxyphenyl)-4-phenyl-isoxazol-5-yl]propanoic acid:

A dry, 250 mL 3-neck round-bottom flask, equipped with a thermometer, magnetic stirring bar, reflux condenser and rubber septum was charged with 1-(3-fluoro-4-methoxyphenyl)-2-phenyl-ethan-1-one oxime from Step 2 (2.00 g, 7.71 mmol) and anhydrous THF (80 mL) under a nitrogen blanket. The solution was cooled to −20° C., and n-butyllithium (1.6N, 12.0 mL) was added, via syringe, over 20 minutes, keeping the reaction temperature <−10° C. The deep red suspension was stirred at −20° C. for 1 hour, warmed to room temperature, and stirred at room temperature for 1 hour. Succinic anhydride (926 mg, 9.26 mmol) was added in one portion, and the yellow reaction was stirred for 16 hours without temperature control. Sulfuric acid (conc., 2.1 mL) was added, and the reaction was warmed to reflux. After 2 hours, the brown mixture was cooled to room temperature, diluted with water (100 mL), and extracted with ether (2×100 mL). The ethereal solution was extracted with dilute sodium hydroxide (2×100 mL), and the combined basic extracts were acidified to pH<2 with hydrochloric acid (conc.). The acidic system was extracted with ether (2×100 mL). This ethereal solution was evaporated under reduced pressure to a residue. The residue was applied to a column of silica gel (200 cc) and eluted (10% methanol in dichloromethane) to yield, upon concentration of the appropriate fractions, a crude solid. The solid was recrystallized from hot ethanol and 0.1N HCl to yield, upon filtration and drying, [3-(3-fluoro-4-methoxyphenyl)-4-phenylisoxazol-5-yl]propanoic acid as ivory colored crystals (367 mg, 14%): mp 129°–131° C. (dec). Mass Spectrum: MH+=342. $^1$H NMR (CDCl$_3$/300 MHz) δ 7.39 (m, 3H), 7.22–7.12 (m, 4H), 6.87 (t, J=8.46 Hz, 1H), 3.88 (s, 3H), 3.09 (t, J=8.05 Hz, 2H), 2.80 (t, J=8.05 Hz, 2H). $^{19}$F NMR(CDCl$_3$/282.2 MHz): −135.466 (m).

Step 4: Preparation of [4-[4-(aminosulfonyl)phenyl]]-3-(3-fluoro-4-methoxyphenyl)isoxazol-5-yl]propanoic acid:

[3-(3-Fluoro-4-methoxyphenyl)-4 phenylisoxazol-5-yl]propanoic acid from Step 3 (250 mg, 0.73 mmol) and sulfuric acid (1 mL) were dissolved in absolute ethanol (10 mL). The colorless solution was warmed to reflux and held for 16 hours. The solution was cooled to room temperature and diluted with water (20 mL). The aqueous solution was extracted with ether (2×50 mL), and the combined ethereal solution was washed with diluted sodium hydroxide (5%, 2×30 mL) and brine (30 mL). The organic solution was dried over magnesium sulfate, filtered and evaporated under reduced pressure to yield an oil. The oil was cooled to 0° C., and cold chlorosulfonic acid (0° C., 12 mL) was added. The reaction was kept at 0° C. under a nitrogen blanket for 2 hours, and was then carefully poured into ice. The ice was extracted with dichloromethane (2×20 mL), then the organic extract was added directly to a vigorously stirred, 0° C. saturated NH$_4$OH solution (40 mL). The biphasic reaction was vigorously stirred at 0° C. for 3 hours. The layers were separated, and the aqueous layer was extracted with dichloromethane (30 mL). The combined organic solution was dried over magnesium sulfate, filtered and evaporated under reduced pressure to yield a crude foam. The foam was dissolved in dioxane (30 mL), aqueous sodium hydroxide (10%, 0.9 mL) was added and the solution was heated to reflux for 1 hour. The solution was cooled to room temperature and diluted with water (20 mL). The aqueous solution was extracted with ether (2×30 mL), then the combined ethereal solution was extracted with dilute sodium hydroxide (5%, 2×30 mL). All of the aqueous phases were combined and acidified with hydrochloric acid (conc.) to pH<2. The acidic aqueous phase was extracted with ether (2×30 mL). The final ether solution was dried over magnesium sulfate, filtered and evaporated under reduced pressure to yield a crude solid. The solid was recrystallized from ethanol/0.1N HCl to yield, upon filtration and drying, [4-[4-(aminosulfonyl)phenyl]-3-(3-fluoro-4-methoxyphenyl)isoxazol-5-yl]propanoic acid as cream-colored crystals (182 mg, 59%): mp=159°–161° C. (dec). $^1$H NMR (CDCl$_3$/300 MHz) δ 7.91 (d, J=8.66 Hz, 2H), 7.34 (d, J=8.66 Hz, 2H), 7.14 (dd, J=11.88, 2.01 Hz), 7.02 (d, J=8.46 Hz), 6.87 (t, J=8.46 Hz, 1H), 3.86 (s, 3H), 3.05 (t, J=7.45 Hz, 2H), 2.74 (t, J=7.45 Hz, 2H). $^{19}$F NMR (CDCl$_3$/282.2 MHz): –135.020 (m).

EXAMPLE 3

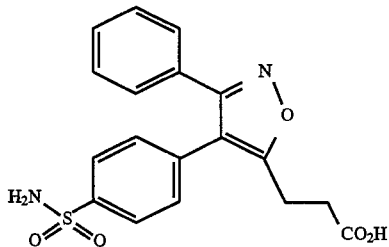

[4-[4-(Aminosulfonyl)phenyl]-3-phenylisoxazol-5-yl]propanoic Acid

Step 1. Preparation of [3,4-diphenylisoxazol-5-yl]propanoic acid.

[3,4-Diphenylisoxazol-5-yl]propanoic acid was prepared in 45% yield from desoxybenzoin oxime (Example 1, Step 1) and succinic anhydride according to the procedure outlined in Example 2, Step 3: mp 123°–125° C. (dec). Anal. Calc'd for $C_{18}H_{15}NO_3$: C, 73.71; H, 5.15; N, 4.78. Found: C, 73.78; H, 5.18; N, 4.72.

Step 2. Preparation of ethyl [4-[4-(aminosulfonyl)phenyl]-5-phenylisoxazol-5-yl]propanoate:

A solution of [3,4-diphenylisoxazol-5-yl]propanoic acid was treated with ethanol in the presence of a catalytic amount of sulfuric acid to prepare the corresponding ethyl ester which was immediately treated with chlorosulfonic acid followed by ammonia according to the procedure from Example 2, Step 4. The crude sulfonamide was purified by flash chromatography eluting with ethyl acetate/hexane (10–50% ethyl acetate) to yield, upon concentration of the appropriate fractions, ethyl [4-[4-(aminosulfonyl)phenyl]-3-phenylisoxazol-5-yl]propanoate as a glassy solid (248 mg, 60%): Mass spectrum: MH+=401. $^1$H NMR (CDCl$_3$/300 MHz) δ 7.93 (d, J=8.46 Hz, 2H); 7.41–7.30 (m, 7H), 4.84 (s, 2H), 4.14 (q, J=7.04 Hz, 2H), 3.12 (t, J=7.45 Hz, 2H), 2.81 (t, J=7.45 Hz, 2H), 1.25 (t, J=7.04 Hz, 3H). This material was used directly in the next step without further purification.

Step 3. Preparation of [4-[4-(aminosulfonyl)phenyl]-3-phenylisoxazol-5-yl]propanoic acid.

Ethyl [4-[4-(aminosulfonyl)phenyl]-3-phenylisoxazol-5-yl]propanoate from Step 2 (198 mg, 0.495 mmol) and aqueous sodium hydroxide (10%, 0.30 mL) were dissolved in dioxane (15 mL). The solution was heated to reflux and held for 16 hours. Upon cooling to room temperature, water (20 mL) was added, and the solution was extracted with ether (2×30 mL). The combined ethereal solution was extracted with dilute sodium hydroxide (5%, 2×30 mL). All of the aqueous phases were combined and acidified with hydrochloric acid (conc.) to pH<2. The acidic aqueous phase was extracted with ether (2×30 mL). The final ether solution was dried over magnesium sulfate, filtered and evaporated under reduced pressure to yield a crude solid. Trituration with dichloromethane yielded crystals. The suspension was cooled to 0° C., filtered, washed with hexane and dried to yield [4-[4-(aminosulfonyl)phenyl]-3-phenylisoxazol-5-yl]propanoic acid as a white crystalline solid (135 mg, 73%): mp 207° C. Mass spectrum: MH+=373. Anal. Calc'd. for $C_{18}H_{16}N_2O_5S$: C, 58.06; H, 4.33; N, 7.52; S, 8.61. Found: C, 57.87; H, 4.35; N, 7.49; S, 8.54.

EXAMPLE 4

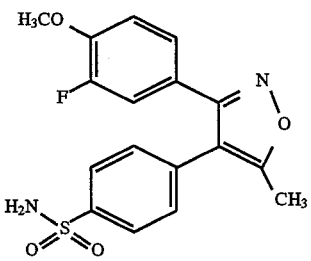

4-[3-(3-Fluoro-4-methoxyphenyl)-5-methylisoxazol-4-yl]benzenesulfonamide

Step 1: Preparation of 3-[3-fluoro-4-methoxyphenyl]-5-methyl-4-phenylisoxazole.

A dry, 250 mL 3-neck round-bottom flask, equipped with a thermometer, magnetic stirring bar, reflux condenser and rubber septum was charged with 1-(3-fluoro-4-methoxyphenyl)-2-phenyl-ethan-1-one oxime (from Example 2, Step 2) (2.50 g, 9.64 mmol) and anhydrous THF (100 mL) under a nitrogen blanket. The solution was cooled to –20° C., and n-butyllithium (1.6N, 15.0 mL) was added, via syringe, over 20 minutes, keeping the reaction temperature <–10° C. The deep red suspension was stirred at –20° C. for 1 hour, warmed to room temperature, and stirred at room temperature for 1 hour. Acetic anhydride (1.1 mL, 11.6 mmol) was added in one portion, and the yellow reaction was stirred for 2 hours without temperature control. The reaction was poured into aqueous hydrochloric acid (1N, 100 mL) and extracted with ethyl acetate (2×100 mL). The combined organic solution was washed once each with aqueous hydrochloric acid (1N, 100 mL) and brine (100 mL), dried over magnesium sulfate, filtered and evaporated under reduced pressure to yield a crude oil. The oil was applied to a column of silica gel (250 ml) and eluted with ethyl acetate/hexane (10–40% ethyl acetate) to yield, upon concentration of the appropriate fractions, 986 mg of 3-(3-fluoro-4-methoxyphenyl)-4-hydrido-5-hydroxy-4-phenyl-5-methylisoxazole. This intermediate was dissolved in tetrahydrofuran (40 mL). Sulfuric acid (conc., 0.9 mL) was added, and the reaction was warmed to reflux. After one hour, the solution was cooled to room temperature, diluted with water (50 mL), and extracted with ethyl acetate (2×50 mL). The combined organic solution was washed with aqueous hydrochloric acid (1N, 50 mL), saturated aqueous sodium bicarbonate (2×50 mL) and brine (50 mL), dried over magnesium sulfate, filtered and evaporated under reduced pressure to yield a crude, dark oil. Washing the oil with 50% dichloromethane in hexane dissolved the compound but did not dissolve the dark impurities. The resulting solution was evaporated under reduced pressure to yield 797 mg (29%) of 3-(3-fluoro-4-methoxyphenyl)-5-methyl-4-phenylisoxazole as a foam. Mass Spectrum: MH+=284. Anal. Calc'd. for $C_{17}H_{14}NO_2F$: C, 72.07; H, 4.98; N, 4.94. Found: C, 72.13; H, 4.98; N, 4.92.

Step 2: Preparation of [3-(3-fluoro-4-methoxyphenyl)-5-methylisoxazol-4-yl]benzenesulfonamide:

Chlorosulfonic acid (8 mL) was cooled to 0° C. 3-(3-Fluoro-4-methoxyphenyl)-5-methyl-4-phenylisoxazole from Step 1 (375 mg, 1.32 mmol) was added in one portion. The brown solution was stirred at 0° C. under a nitrogen blanket for 2 hours, then added dropwise to ice (50 mL). The ice was extracted with dichloromethane (2×30 mL), and the organic extracts were added directly to a 0° C. saturated aqueous $NH_4OH$ solution. The biphasic reaction was vigorously stirred at 0° C. for 2 hours, then the layers were separated. The aqueous solution was extracted with dichloromethane, the combined organic solutions were dried over magnesium sulfate, filtered and evaporated under reduced pressure to yield a crude solid. The solid was recrystallized from ethanol and water to yield, upon filtration and drying, 4-[3-(3-fluoro-4-methoxyphenyl)-5-methylisoxazol-4-yl]benzenesulfonamide as ivory colored crystals (275 mg, 55%): mp 175° C. (dec). Mass Spectrum: MH+=363. Anal. Calc'd. for $C_{17}H_{15}N_2O_4FS$: C, 56.47; H, 4.17; N, 7.73; S, 8.85. Found: C, 56.47; H, 4.19; N, 7.66; S, 8.81.

Proceeding in a like manner but replacing desoxybenzoin with other appropriately substituted ketones, the following compounds were prepared:

4a) 4-[3-(4-chlorophenyl)-5-methyl-isoxazol-4-yl]benzenesulfonamide: mp 162°–164° C. $^1H$ NMR ($CDCl_3$) 7.97 (d, 2H, J=8.46 Hz), 7.33–7.26 (m, 7H), 2.48 (s, 3H). Elemental analysis Calc'd. for $C_{16}H_{13}N_2O_3SCl$: C, 55.1; H, 3.76; N, 8.03. Found: C, 55.12; H, 3.78; N, 8.03.

4b) 4-[3-(4-fluorophenyl)-5-methyl-isoxazol-4-yl]benzenesulfonamide: mp 152°–156° C. $^1H$ NMR ($CDCl_3$) 2.48 (s, 3H), 4.84 (bs, 2H), 7.04 (t, 1H, J=8.6 Hz), 7.33–7.40 (m, 4H), 7.94 (d, 2H, J=8.4). High resolution mass spectrum Calc'd for $C_{16}H_{13}FN_2O_3S$: 333.0709. Found: 333.0704.

4c) 4-[3-(3-fluoro-4-methylphenyl)-5-methyl-isoxazol-4-yl]benzenesulfonamide: mp 146°–150° C. $^1H$ NMR ($CDCl_3$) 2.24 (s, 3H), (2.48 (s, 3H), 4.97 (bs, 2H), 6.93 (t, 1H, J=9.1 Hz), 7.04 (m, 1H), 7.26–7.37 (m, 3H), 7.94 (d, 2H, J=8.3). High resolution mass spectrum Calc'd for $C_{17}H_{15}FN_2O_3S$: 347.0866. Found: 347.0865. Anal. Calc'd. for $C_{17}H_{15}FN_2O_3S$: C, 58.95; H, 4.37; N, 8.03. Found: C, 58.09; H ,4.47; N, 8.03.

4d) 4-[3-(3-aminosulfonyl-4-methoxyphenyl)-5-methyl-isoxazol-4-yl]benzenesulfonamide.

4e) 4-[3-(3-chloro-4-methylphenyl)-5-methyl-isoxazol-4-yl]benzenesulfonamide: mp 120°–122° C. $^1H$ NMR ($CD_3OD$) 2.30 (s, 3H), 2.48 (s, 3H) 4.84 (bs, 2H), 7.11 (m, 1H), 7.33–7.40 (m, 4H), 7.92 (d, 2H, J=8.4). High resolution mass spectrum Calc'd for $C_{17}H_{15}FN_2O_3S$: 363.0570. Found: 363.0584. Elemental analysis. Calc'd for $C_{17}H_{15}ClN_2O_3S$: C, 56.28; H, 4.17; N, 7.72. Found: C, 56.02; H, 4.38; N, 7.54.

4f) 4-[5-methyl-3-(3-pyridyl)isoxazol-4-yl]benzenesulfonamide: mp 110°–115° C. (dec). $^1H$ NMR ($CDCl_3$) 8.57 (br s, 1H), 8.47 (s, 1H), 7.88, 7.24 (AB quartet, 4H), 7.51–7.41 (m, 2H), 2.43 (s, 3H). Mass spectrum $M^+H$ 316.

4g) 4-[5-methyl-3-(4-pyridyl)-isoxazol-4-yl]benzenesulfonamide: mp 108°–110° C. (dec). $^1H$ NMR ($CDCl_3$) 8.51 (d, 2H, J=6.0 Hz), 7.9 (d, 2H, J=8.46 Hz), 7.30–7.26 (m, 4H), 6.11 (s, 2H), 2.44 (s, 3H). Mass spectrum $M^+H$ 316. Anal. Calc'd. for $C_{15}H_{13}N_3O_3SO_3.H_2O$: C, 54.05; H, 4.54; N, 12.62. Found: C, 53.65; H, 4.08; N, 12.42.

4h) 4-[3-(3-fluorophenyl)-5-methyl-isoxazol-4-yl]benzenesulfonamide: mp 130°–136° C. (dec). $^1H$ NMR ($CDCl_3$) 7.95 (d, 2H, J=8.5 Hz), 7.33 (d, 2H), 7.33–7.11 (m, 4H), 2.50 (s, 3H). Mass spectrum $M^+H$ 333. Anal. Calc'd. for $C_{16}H_{13}N_2O_3SF$: C, 57.82; H, 3.94; N, 8.43. Found: C, 57.42; H, 4.57; N, 7.50.

EXAMPLE 5

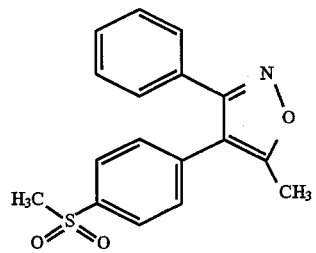

5-Methyl-4-[4-(methylsulfonyl)phenyl]-3-phenylisoxazole

Step 1. Preparation of 1-phenyl-2-[4-(methylthio)phenyl]ethan-1-one.

This ketone was prepared from the Friedel Crafts acylation of benzene with 4-methylthiophenylacetyl chloride in the presence of aluminum chloride: $^1H$ NMR ($CDCl_3$/300 MHz) δ 7.92 (d, J=8.66 Hz, 2H), 7.32–7.22 (m, 7H), 4.24 (s, 2H), 2.51 (s, 3H).

Step 2. Preparation of 1-phenyl-2-[4-(methylthio)phenyl]-ethan-1-one oxime.

This oxime was prepared from 1-phenyl-2-[4-(methylthio)phenyl]-ethan-1-one (Step 1) and hydroxylamine in 80% yield by the method outlined in Example 1, Step 1: $^1H$ NMR ($CDCl_3$/300 MHz) δ 7.54 (d, J=8.66 Hz, 2H), 7.32–7.17 (m, 7H), 4.19 (s, 2H), 2.36 (s, 3H).

Step 3. Preparation of 5-methyl-4-[4-(methylthio)phenyl]-3-phenylisoxazole:

5-Methyl-4-[4-(methylthio)phenyl]-3-phenylisoxazole was prepared in 48% yield from the reaction of 1-phenyl-2-[4-(methylthio)phenyl]-ethan-1-one oxime (Step 2) and acetic anhydride according to the procedure outlined in Example 4, Step 1: Mass Spectrum: MH+=282. High resolution mass spectrum Calc'd. for $C_{17}H_{15}NOS$: 281.0874. Found: 281.0875. Anal. Calc'd. for $C_{17}H_{15}NOS$: C, 72.57; H, 5.37; N. 4.98; S, 11.39. Found: C, 72.56; H, 5.41; N, 5.00; S, 11.34.

Step 4. Preparation of 5-methyl-4-[4-(methylsulfonyl)phenyl]-3-phenylisoxazole:

5-Methyl-4-[4-(methylthio)phenyl]-3-phenylisoxazole from Step 3 (100 mg, 0.355 mmol) was dissolved in methanol (20 mL). Oxone® (0.765 g, 1.24 mmol) and water (2 mL) were added, and the suspension was stirred at room temperature for 2 hours. Water was added (30 mL) and the resulting suspension was cooled to 0° C. and held for 30 minutes whereupon the product crystallized. The product was isolated by filtration, washed with water and dried to yield 5-methyl-4-[4-(methylsulfonyl)phenyl]-3-phenylisoxazole (32 mg, 29%): mp 54°–56° C. Mass Spectrum: MLi+=320. High resolution mass spectrum Calc'd for $C_{17}H_{15}NO_3S$: 313.077. Found: 313.078.

EXAMPLE 6

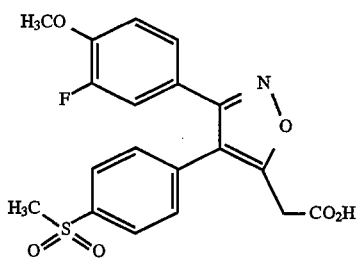

[3-[3-Fluoro-4-methoxyphenyl]-4-[4-(methylsulfonyl)phenyl]isoxazol-5-yl]acetic Acid Step 1. Preparation of 1-(3-fluoro-4-methoxyphenyl)-2-[4-(methylthio)phenyl]-ethan-1-one.

1-(3-Fluoro-4-methoxyphenyl)-2-[4-(methylthio)phenyl]-ethan-1-one was prepared by Friedel Crafts acylation of 2-fluoroanisole with 4-(methylthio)phenylacetyl chloride in the presence of aluminum chloride: $^1$H NMR (CDCl$_3$/300 MHz) δ 7.80–7.70 (m, 2H), 7.24–7.15 (m, 4H), 6.98 (t, J=8.26 Hz), 4.17 (s, 2H), 3.95 (s, 3H), 2.46 (s, 3H). $^{19}$F NMR (CDCl$_3$/282.2 MHz): −134.804 (m).

Step 2. Preparation of 1-(3-fluoro-4-methoxyphenyl)-2-[4-(methylthio)phenyl]-ethan-1-one oxime.

1-(3-Fluoro-4-methoxyphenyl)-2-[4-(methylthio)phenyl]-ethan-1-one oxime was prepared in yield by treatment of 1-(3-fluoro-4-methoxyphenyl)-2-[4-(methylthio)phenyl]-ethan-1-one from Step 1 with hydroxylamine: $^1$H NMR (CDCl$_3$/300 MHz) δ 7.40 (dd, J=12.69, 2.22 Hz, 1H), 7.30 (d, J=8.66 Hz, 1H), 7.18–7.12 (m, 4H), 6.88 (dd, J=8.66, 8.46 Hz, 1H), 4.10 (s, 2H), 3.87 (s, 3H), 2.43 (s, 3H).

Step 3. Preparation of 3-(3-fluoro-4-methoxyphenyl)-5-methyl -4-[4-(methylthio)phenyl]isoxazole:

3-(3-Fluoro-4-methoxyphenyl)-5-methyl-4-[4-(methylthio)phenyl]isoxazole was prepared in 30% yield from 1-(3-fluoro-4-methoxyphenyl)-2-[4-(methylthio) phenyl]-ethan-1-one oxime from Step 2 and acetic anhydride by the procedure described in Example 4, Step 1 and used directly in the next step.

Step 4. Preparation of [3-[3-fluoro-4-methoxyphenyl]-4-[4-(methylsulfonyl)phenyl]isoxazol-5-yl]acetic acid.

3-(3-Fluoro-4-methoxyphenyl)-5-methyl-4-[4-(methylthio)phenyl]isoxazole (326 mg, 0.99 mmol) was charged to an oven-dried 100 mL 3-neck round-bottom flask equipped with a thermometer, nitrogen inlet, rubber septum and a magnetic stirring bar. Anhydrous THF (35 mL) was added, and the solution was cooled to −78° C. under a dry nitrogen blanket. To this solution, n-butyllithium (1.6N in hexane; 0.74 mL) was added, via syringe over approximately 3 minutes, keeping the reaction temperature <−75° C. The deep red suspension was stirred at −78° C. for 1 hour. Simultaneously, anhydrous tetrahydrofuran (80 mL) was cooled to −78° C. in an oven-dried 250 mL round-bottom flask. This solvent was saturated with carbon dioxide gas.

The red reaction solution was quenched into the carbon dioxide-saturated THF. The yellow reaction was warmed to room temperature over 2 hours, then diluted with water (50 mL) and ether (80 mL). The solution was extracted with aqueous sodium hydroxide (5%, 2×50 mL), and the combined aqueous solution was acidified to pH<2 with aqueous hydrochloric acid (conc.). The acidic solution was extracted with dichloromethane (2×50 mL). The combined organic solution was dried over magnesium sulfate, filtered and evaporated under reduced pressure to a crude solid. The solid was dissolved in methanol (20 mL) in a 100 mL round-bottom flask equipped with a magnetic stirring bar and a nitrogen gas inlet. Oxone® (2.13 g, 3.47 mmol) and water (3 mL) were added, the suspension was stirred at room temperature for 2 hours, warmed to reflux and held for an additional 2 hours. Upon cooling to room temperature, water (35 mL) and aqueous hydrochloric acid (6N, 1 mL) were added. The resulting suspension was cooled to 0° C., held for 30 minutes, filtered and washed with cold water to yield, upon drying, [3-(3-fluoro-4-methoxyphenyl)-4-[4-(methylsulfonyl)phenyl]isoxazol-5-yl]acetic acid as white crystals (173 mg, 43%): mp 89° C. Mass spectrum: MH+= 406. Anal. Calc'd. for $C_{19}H_{16}NO_6FS$: C, 56.29; H, 3.98; N, 3.46; S, 7.91. Found: C, 56.22; H, 4.00; N, 3.44; S, 7.85.

EXAMPLE 7

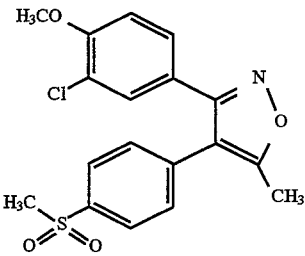

3-(3-Chloro-4-methoxyphenyl)-5-methyl-4-[4-methylsulfonylphenyl]isoxazole

Step 1. Preparation of 3-Chloro-4-methoxyacetophenone.

A 5 L round bottomed flask equipped with mechanical stirrer, reflux condenser, constant pressure addition funnel and nitrogen inlet was charged with anhydrous aluminum chloride (281 g, 2.104 mol) and 1 L of ethanol-free chloroform. The solution was maintained at 0° C. with an ice bath while a solution of acetyl chloride (162 g, 2.28 mol) in 300 mL of chloroform was added from the addition funnel over 25 minutes. To this solution was added 2-chloroanisole (250 g, 1.75 mol) in 250 mL of chloroform over 1 hour. The solution was stirred at room temperature for 16 hours and the contents of the flask were poured into a mixture of ice and water. The phases were separated and the aqueous phase extracted with dichloromethane and combined with the original organic phase, dried over anhydrous MgSO$_4$, filtered and concentrated in vacuo to afford a solid that was crystallized from dichloromethane/hexane to give 3-chloro-4-methoxyacetophenone (246 g, 76%) that was used directly in the next step without further purification.

Step 2. Preparation of 3-chloro-4-methoxyphenylacetic acid.

A mixture of 3-chloro-4-methoxyacetophenone from Step 1 (10.0 g, 54.2 mmol) and boron trifluoride etherate complex (26.6 mL, 0.216 mol) in 20 mL of methanol was added to a suspension of lead tetraacetate (24 g, 54.2 mmol) in 50 mL of toluene. The mixture was stirred at room temperature for 16 hours, treated with 50 mL of water and poured into a separatory funnel. The phases were separated and the aqueous phase washed with toluene. The toluene solution was dried over anhydrous MgSO$_4$, filtered and concentrated in vacuo to provide an oil that was dissolved in 40 mL of dioxane and treated with excess 2.5N sodium hydroxide solution. The solution was stirred at room temperature for 2 hours and concentrated in vacuo. The residue was extracted with dichloromethane and the aqueous phase acidified with concentrated HCl. The acidic solution was extracted with dichloromethane. The dichloromethane extract was dried over anhydrous MgSO$_4$, filtered and concentrated in vacuo to afford pure 3-chloro-4-methoxyphenylacetic acid (9.11 g, 84%) that was used directly in the next step.

Step 3. Preparation of 2-(3-chloro-4-methoxyphenyl)-3-[4-(methylthio)phenyl]-2-propenoic acid.

A mixture of 3-chloro-4 methoxyphenylacetic acid from Step 2 (4.50 g, 22.4 mmol), 4-methylthiobenzaldehyde (2.70 g, 20.4 mmol) and triethylamine (2.8 mL, 20.4 mmol) were dissolved in 40 mL of acetic anhydride and heated to reflux for 3 hours. The solution was cooled to 110° C. and treated cautiously with 70 mL of water and cooled to room temperature, whereupon crystals of 2-(3-chloro-4-methoxyphenyl)-3-[4-(methylthio)phenyl]-2-propenoic acid formed that were isolated by filtration and air dried to afford 5.68 g (75%) of pure compound which was used directly in the next step.

Step 4. Preparation of 1-(3-chloro-4-methoxyphenyl)-2-[4-(methylthio)phenyl]-ethan-1-one.

A solution of 1-(3-chloro-4 methoxyphenyl)-3-[4-(methylthio)phenyl]propenoic acid from Step 3 (5.00 g, 14.9 mmol) and triethylamine (2.20 g, 15.7 mmol) in 50 mL of toluene was cooled to 0° C. and treated with diphenylphosphoryl azide (3.20 g, 14.9 mmol) via syringe. The solution was maintained at 0° C. for 30 minutes and then diluted with water. The phases were separated and the aqueous phase washed with ether. The original toluene solution was combined with the ethereal extract, dried over anhydrous MgSO$_4$, filtered and concentrated to remove the ether. The remaining toluene solution was heated to 115° C. for 90 minutes, treated with tert-butyl alcohol (1.50 g, 16.4 mmol) and maintained at this temperature for an additional 30 minutes. The solution was cooled to 90° C., treated with 1.4 mL of concentrated HCl and cooled to room temperature. The solution was washed with saturated aqueous NaHCO$_3$, and with brine and dried over anhydrous MgSO$_4$, filtered and concentrated to give 1-(3-chloro-4-methoxyphenyl)-2-[4-(methylthio)phenyl]-ethan-1-one as a solid that was used directly in the next step: $^1$H NMR (CDCl$_3$/300 MHz) δ 7.90 (d, J=8.66 Hz, 2H), 7.29–7.24 (m, 3H), 7.11 (dd, J=8.46, 2.21 Hz, 1H), 6.88 (d, J=8.46 Hz, 1H), 4.19 (s, 2H), 3.86 (s, 3H), 2.55 (s, 3H).

Step 5. Preparation of 1-(3-chloro-4-methoxyphenyl)-2-[4-(methylthio)phenyl]-ethan-1-one oxime.

1-(3-Chloro-4-methoxyphenyl)-2-[4-(methylthio)phenyl]-ethan-1-one oxime was prepared in 41% yield from the reaction of 1-(3 chloro-4-methoxyphenyl)-2-[4-(methylthio)phenyl]-ethan-1-one from Step 4 with hydroxylamine by the method outlined in Example 1, Step 1: $^1$H NMR (CDCl$_3$/300 MHz) δ 7.69 (d, J=2.22 Hz, 1H), 7.47 (dd, J=8.66, 2.22 Hz, 1H), 7.21–7.16 (m, 4H), 6.86 (d, J=8.66 Hz, 1H), 4.11 (s, 2H), 3.89 (s, 3H), 2.44 (s, 3H).

Step 6. Preparation of 3-(3-chloro-4-methoxyphenyl)-4-[4-methylsulfonylphenyl]-5-methylisoxazole 3-(3-Chloro-4-methoxyphenyl)-5-methyl-4-[4-(methylthio)phenyl]isoxazole was prepared in 26% yield from 1-(3-chloro-4-methoxyphenyl)-2-[4-(methylthio)phenyl]-ethan-1-one oxime from Step 5 and acetic anhydride by the method described in Example 4, Step 1 and then oxidized to 3-(3-chloro-4 methoxyphenyl)-5-methyl-4-[4-methylsulfonylphenyl]isoxazole with Oxone® by the method described in Example 5, Step 4: Mass spectrum: MLi+=384. High resolution mass spectrum Calc'd. For C$_{18}$H$_{16}$ClNO$_4$S: 378.0567. Found: 378.0573.

EXAMPLE 8

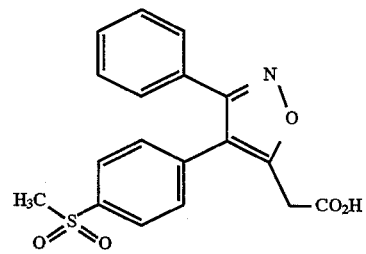

[4-[4-(Methylsulfonyl)phenyl]-3-phenyl)isoxazol-5-yl]acetic Acid

Step 1. Preparation of [4-[4-(methylthio)phenyl]-3-phenylisoxazol-5-yl]acetic acid.

[4-[4-(Methylthio)phenyl]-3-phenylisoxazol-5-yl]acetic acid was prepared in 35% yield by carboxylation of 4-[4-(methylthio)phenyl]-5-methyl-3-phenylisoxazole [Example 5, Step 3] according to the procedure detailed in Example 6, Step 4: Mass spectrum: MH+=326. High resolution mass spectrum Calc'd. for C$_{18}$H$_{15}$NO$_3$S: 325.0773. Found: 325.0776.

Step 2. Preparation Of [4-[4-(methylsulfonyl)phenyl]-3-phenylisoxazol-5-yl]acetic acid.

[4-[4-(Methylsulfonyl)phenyl]-3-phenyl)isoxazol-5-yl]acetic acid was prepared in 80% yield from [4-[4-(methylthio)phenyl]-3-phenylisoxazol-5-yl]acetic acid (Step 1) by oxidation with Oxone® according to the procedure detailed in Example 5, Step 4: Mass spectrum: MH+= 326. High resolution mass spectrum Calc'd. For C$_{18}$H$_{15}$NO$_5$S: 358.0749. Found: 358.0769.

EXAMPLE 9

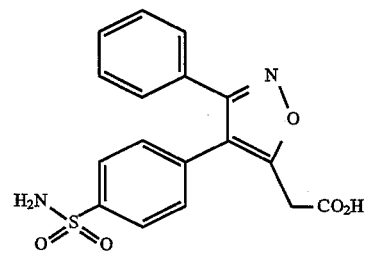

[4-[4-(Aminosulfonyl)phenyl]-3-phenylisoxazol-5-yl]acetic Acid

Step 1. Preparation of 3,4-diphenyl-5-methylisoxazole.

A solution of desoxybenzoin keto-oxime (Example 1, Step 1) (6.00 g, 28.40 mmol) in anhydrous tetrahydrofuran (80 mL) was cooled to −20° C. in an oven-dried 250 mL three-neck round-bottom flask equipped with a thermometer, nitrogen gas inlet, rubber septum and provisions for magnetic stirring. To this cold solution, n-butyllithium (1.6N in hexanes, 44.4 mL) was added, via syringe, over 35 minutes, such that the reaction temperature remained at or below −10° C. The deep red solution was stirred at −10° C. for 1 hour, warmed to room temperature, then stirred at room temperature for an additional hour. Acetic anhydride (3.2 mL, 34.1 mmol) was added in one portion, and the resulting suspension was stirred without temperature control for 2 hours. Water (100 mL) was added, and the solution was poured into 1N HCl (100 mL) and extracted with ethyl acetate (2×200 mL). The combined organic solution was washed with HCl (1N HCl, 100 mL) and brine (100 mL), dried over anhydrous $MgSO_4$ and filtered. The resulting solution was concentrated in vacuo to yield a crude oil. The oil was applied to a column of silica gel and eluted with ethyl acetate/hexane (10–50% ethyl acetate) to yield, upon concentration of the appropriate fractions, 5.0 g of 3,4-diphenyl-4-hydrido-5-hydroxy-5-methylisoxazole. A 100 mL round bottomed flask equipped with reflux condenser was charged with 3,4-diphenyl-4-hydrido-5-hydroxy-5-methylisoxazole (5.00 g, 19.74 mmol), 300 mg of concentrated $H_2SO_4$ and 30 mL of toluene. The solution was heated to reflux for 1 hour, poured into a separatory funnel and washed with water. The toluene solution was dried over anhydrous $MgSO_4$, filtered, and concentrated in vacuo and the residue used directly in the next step without further purification.

Step 2. Preparation of (3,4-diphenylisoxazol-5-yl)acetic acid:

(3,4-Diphenylisoxazol-5-yl)acetic acid was prepared in 53% yield by carboxylation of 3,4-diphenyl-5-methyl-isoxazole (Step 1) according to the procedure outlined in Example 6, Step 4: Mass spectrum: MH+=280. High resolution mass spectrum Calc'd. for $C_{17}H_{13}NO_3$: 280.0894. Found: 280.0897. Anal. Calc'd. for $C_{17}H_{13}NO_3$: C, 73.11; H, 4.69; N, 5.01. Found: C, 72.91; H, 4.73; N, 4.97.

Step 3. Preparation of [4-[4-(aminosulfonyl)phenyl]-3-phenylisoxazol-5-yl]acetic acid:

[4-[4-(Aminosulfonyl)phenyl]-3-phenylisoxazol-5-yl] acetic acid was prepared in 60% yield by chlorosulfonation followed by ammonolysis of 1-(3,4-diphenylisoxazol-5-yl) acetic acid according to the procedure outlined in Example 2, Step 4: mp 61° C. Mass spectrum: MH+=359.

EXAMPLE 10

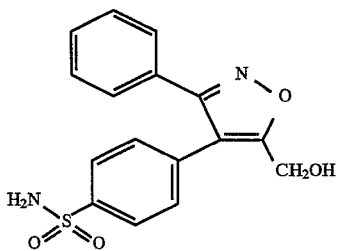

4-[5-Hydroxymethyl-3-phenylisoxazol-4-yl] benzenesulfonamide

4-[5-Methyl-3-phenyl-4-yl]benzenesulfonamide (Example 1) (20.965 g, 66.69 mmol) and THF (1.4 L) were cooled to −78° C. (dry-ice/acetone bath) and a premeasured volume of n-BuLi (167 mL, 266.76 mmol) in a 250 mL round bottomed flask was added via cannula causing the reaction solution to become bright red. After 15 minutes the dry ice/acetone bath was replaced with a NaCl/ice/water bath and the reaction warmed to −5° C. over 15 minutes and was maintained at −5° C. for 30 more minutes. The NaCl/ice/$H_2O$ bath was replaced with a dry ice/acetone bath and the reaction chilled to −71° C. Oxygen was added via two 14 gauge needles (ca. 4 psi) and a similar outlet provided. Within 10 minutes the reaction, formerly a red suspension, became an ocre-yellow suspension. Oxygen addition was continued for 30 more minutes. The oxygen line and vents were removed and trimethyl phosphite (67 mL, 566.97 mmol) was added via syringe. After 15 minutes, the septum was removed and a solution of HOAc (125 mL) and $H_2O$ (125 mL) was added in one portion causing the solution to become a hazy bright yellow and the reaction temperature to rise to −50° C. The dry ice bath was removed and the reaction was warmed to room temperature. Brine (700 mL) and 1N HCl (134 mL) were added and stirred for 15 minutes. Ethyl acetate (700 mL) was added and the layers were separated in a separatory funnel. The aqueous phase was washed with ethyl acetate (150 mL) and the organic layers combined. The organic layer was washed with water, $NaHCO_3$ (5×100 mL) and brine, dried over anhydrous $MgSO_4$, and filtered. The resulting organic phase was diluted with toluene (125 mL) and concentrated in vacuo three times yielding a brown viscous oil. The crude product was purified by flash chromatography (silica gel, 10×18 cm column, hexane/ethyl acetate (1/2) with a step gradient to hexane/ethyl acetate (1/2)) yielding a yellow solid (11.25 g). The product was dissolved in ethyl acetate (500 mL) and acetone (60 mL). Partial concentration of this solution and addition of hexane yielded a yellow solid which was collected by vacuum filtration. This solid was dissolved in a minimum of acetone and added to hot $H_2O$ (800 mL at 70° C.) yielding the desired product as a very fine crystalline yellow product (7.89 g, 36%): mp 188°–189° C. $^1$H NMR (DMSO $d_6$) δ 7.81 (d, J=8.26 Hz, 2 H), 7.26–7.55 ( m, 9 H), 5.77 (t, J=4.84, 1 H), 4.54 (d, J=4.84, 2 H). Anal. Calc'd. for $C_{16}H_{14}N_2O_4S_1$: C, 58.17; H, 4.27; N, 8.48. Found: C, 58.22; H, 4.31; N, 8.50. Mass spectrum: M+H: 331.

EXAMPLE 11

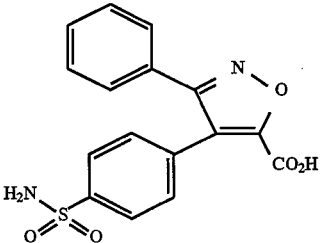

[4-[4-(Aminosulfonyl)phenyl]-3-phenylisoxazol-5-yl]carboxylic Acid

To a solution of 4-[5-hydroxymethyl-3-phenyl-4-yl] benzenesulfonamide (Example 10) (0.64 g, 1.94 mmol) in acetone at −78° C. (dry ice-acetone bath) was added carefully Jones reagent (0.7 mL of 2.44M $CrO_3$ in aqueous $H_2SO_4$ solution). The reaction was warmed to 0° C. and an additional 0.7 mL (2.44M $CrO_3$ in aqueous $H_2SO_4$ solution) was added. The reaction was warmed to room temperature and stirred overnight. Isopropanol (2 mL) was added and was stirred for 2 hour. The reaction was diluted with ethyl acetate, washed with $H_2O$, dried over anhydrous $MgSO_4$, filtered through Celite® and concentrated in vacuo yielding a solid. Recrystallization of this solid from toluene yielding the desired product (0.075 g, 11%) as a tan solid: mp 300° C. $^1$H NMR (DMSO $d_6$) δ 7.70 (d, J=8.46 Hz, 2H), 7.08–7.50 (m, 9H).

EXAMPLE 12

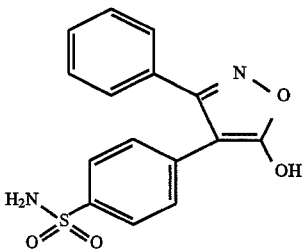

4-[5-Hydroxy-3-phenyl-4-isoxazolyl]benzenesulfonamide

Step 1. Preparation of 3,4-diphenylisoxazolin-5-one.

To a stirred solution of the deoxybenzoin oxime (50.59 g, 239 mmol) in anhydrous THF (1 L) in a 2000 mL 2-neck round bottomed flask fitted with septum, under nitrogen atmosphere, and chilled to −78° C. (dry ice/acetone bath) was added n-BuLi (375 mL of 1.6M in hexanes, 599 mmol) via cannula over 15 minutes. After twenty minutes at −78° C., the dry ice/acetone bath was replaced with a NaCl/ice/H$_2$O and the reaction was warmed to 0° C. over 1 hour. The NaCl/ice/H$_2$O bath was replaced with a dry ice/acetone bath. When −78° C. was reached, the reaction solution was transferred via cannula to a 4 L Erlenmeyer flask filled with 1500 cc of powdered dry ice and the resulting yellow mixture was let stand overnight at room temperature. The clear, straw colored solution was transferred to a 3 L round bottomed flask, and 700 mL of 3N HCl was added. The reaction was heated to reflux for 1 hour and cooled to room temperature. The reaction was diluted with brine (500 mL) and the layers were separated in a separatory funnel. The aqueous layer was extracted with dichloromethane/ethyl acetate (2/1) (400 mL). The organic layers were combined and washed with brine (200 mL), dried over anhydrous MgSO$_4$, filtered and concentrated yielding a brown solid. The solid was re-dissolved in warm THF and hexanes were added yielding a fluffy off-white crystalline solid (30.4 g, 54%). A second crop was obtained (12.66 g, 22 %): mp 162°–163° C. (dec.). This material was suitable for use without further purification.

Step 2. Preparation of 4-[5-hydroxy-3-phenyl-4-yl]benzenesulfonamide.

3,4-Diphenylisoxazolin-5-one from step 1 (15.6 g, 65.75 mmol) was added carefully to ClSO$_3$H (160 mL) in a 250 mL round bottomed flask chilled in a NaCl/ice bath. After 2 hours, the crude reaction mixture was carefully poured over ice, yielding the crude sulfonyl chloride as a precipitate which was collected by vacuum filtration. The solid was dissolved in dichloromethane yielding two phases which were separated, and the organic phase dried over anhydrous MgSO$_4$. This clear pale yellow solution was slowly added to a chilled (0° C.) saturated solution of NH$_3$, in dichloromethane. The resulting suspension was diluted with CH$_3$OH and was washed with KHSO$_4$ (0.25M aq soln.). The organic layer was dried over anhydrous MgSO$_4$, filtered and concentrated in vacuo yielding a tan solid which was collected by vacuum filtration. This solid was dissolved in a minimum of 1N NaOH solution, filtered, and washed with dichloromethane. The aqueous layer was acidified with concentrated HCl yielding and off-white solid (3.70 g, 18%): mp 207° C. (dec.). $^1$H NMR (D$_2$O with NaOD) δ 7.48 (d, J=8.46 Hz, 2 H), 7.38–7.20 (m, 5 H), 7.14, (d, J=8.26, 2 H). The methanolic/aqueous KHSO$_4$ wash phase, upon partial evaporation yielded additional desired product as a tan solid (8.94 g, 43%).

EXAMPLE 13

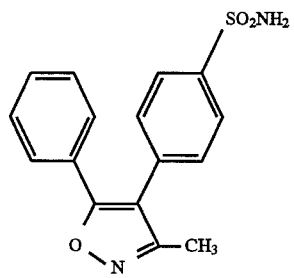

4-[3-Methyl-5-phenyl-4-isoxazolyl]benzenesulfonamide

Step 1. Preparation of 1,2-diphenyl-1-butene-3-one oxime.

A solution of 1,2-diphenyl-1-butene-3-one (1.5 g, 7 mmol) in EtOH (15 ml) and was added to a solution of hydroxylamine hydrochloride (500 mg, 7 mmol) and NaHCO$_3$ (1 g) in water (7 ml). The mixture was heated to reflux for 5 hours at which time thin layer chromatography indicated the reaction was incomplete. Additional hydroxylamine hydrochloride (500 mg, 7 mmol) was added and heating at reflux was continued overnight. The reaction was cooled, poured into water (100 ml) and extracted with ethyl acetate. The combined organic layers were dried over sodium sulfate, filtered and the filtrate concentrated in vacuo. The crude material was chromatographed on silica gel using 5% ethyl acetate in toluene as the eluant to give 450 mg (30%) of the desired oxime as a crystalline solid, m.p. 138°–141°. Anal. Calc'd. for C$_{16}$H$_{15}$NO: C, 80.98; H, 6.37; N, 5.90. Found: C, 80.79; H, 6.25; N, 6.09.

Step 2. Preparation of 3,4-diphenyl-5-methylisoxazole

To a solution of oxime from Step 1 (450 mg, 1.9 mmol) and sodium bicarbonate (650 mg, 7.7 mmol) in tetrahydrofuran (6 ml) and water (6 ml) in a vessel wrapped in aluminum foil was added a solution of potassium iodide (1.1 g, 6.6 mmol) and iodine (525 mg, 2 mol) in water (4 ml). The reaction was heated to reflux for 7 hours and stirred at room temperature overnight. Saturated aqueous sodium bisulfite solution (5 ml) was added and the reaction mixture was extracted with ethyl acetate. The combined organic layers were dried over sodium sulfate and the crude material was isolated after filtration and concentration of the filtrate. Chromatography on silica gel using toluene as the eluant gave 290 mg (57%) of the isoxazole as an oil which crystallized on standing: mp 92°–94° C. Anal. Calc'd for C$_{16}$H$_{13}$NO: C, 81.31; H, 5.57; N, 5.95. Found: C, 81.31, H, 5.71; N, 6.18.

Step 3. Preparation of 4-[3-methyl-5-phenyl-4-isoxazolyl]benzenesulfonamide.

A solution of the isoxazole from step 1 (250 mg, 1.1 mmol) in chlorosulfonic acid (1 ml) was stirred at 0° for 3 hours. The reaction was cautiously added to concentrated ammonium hydroxide (6 ml) in the cold (0° C.). The resultant reaction mixture was stirred at 0° for 1 hour. The reaction was cautiously diluted with water and extracted with ethyl acetate.. The combined organic layers were dried over sodium sulfate, filtered, and the filtrate concentrated in vacuo to give the crude product. This material was chromatographed on silica gel using 25% ethyl acetate in toluene as the eluant to give the desired sulfonamide as a crystalline solid (110 mg, 40%): mp 85°–87° C. Anal. Calc'd. for C$_{16}$H$_{14}$N$_2$O$_3$S: C, 61.13; H, 4.49; N, 8.91; S, 10.20. Found: C, 60.88; H, 4.61; N, 8.55; S, 10.40.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs, in Non-steroidal Anti-Inflammatory Drugs*, (J. Lombardino, ed. 1985)). The % inhibition shows the % decrease from control paw volume determined in this procedure and the data for selected compounds in this invention are summarized in Table I.

Rat Carrageenan-induced Analgesia Test

The rat carrageenan analgesia test was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE 1

| | RAT PAW EDEMA<br>% Inhibition<br>@ 10 mg/kg body weight | ANALGESIA<br>% Inhibition<br>@ 10 mg/kg body weight |
|---|---|---|
| Example 1 | 29 | 33 |

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at $-80°$ C. before being assayed for COX activity.

b. Assay for COX-1 and COX-2 activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | COX-2 $ID_{50}$ μM | COX-1 $ID_{50}$ μM |
|---|---|---|
| 1 | <0.1 | >100 |
| 1a | <0.1 | 17.4 |
| 1b | <0.1 | 13.2 |
| 1c | <0.1 | 6.2 |
| 1d | <0.1 | 25.8 |
| 1e | <0.1 | 37.7 |
| 1f | 0.2 | 54 |
| 1g | <0.1 | >100 |
| 1h | <0.1 | 4.7 |
| 1i | <0.1 | 8.6 |
| 1k | <0.1 | >100 |
| 1l | <0.1 | 50.7 |
| 1m | 1.5 | >100 |
| 1n | 51 | >100 |
| 1o | <0.1 | >100 |
| 1p | 0.1 | >100 |
| 2 | 0.9 | 17.4 |
| 3 | 2.6 | 0.6 |
| 4 | 3 | >100 |
| 4a | <0.1 | 90.5 |
| 4b | <0.1 | >100 |
| 4c | <0.1 | 66.5 |
| 4d | <0.1 | 44 |
| 4e | | |
| 4f | 2 | >100 |
| 4g | >100 | >100 |
| 5 | 4.0 | >100 |
| 6 | 35.7 | >100 |
| 7 | 86.7 | >100 |
| 8 | >100 | >100 |
| 9 | 1.4 | >100 |

TABLE II-continued

| Example | COX-2 ID$_{50}$ μM | COX-1 ID$_{50}$ μM |
| --- | --- | --- |
| 10 | 0.2 | >100 |
| 11 | 35 | |
| 12 | 2.5 | >100 |
| 13 | <0.1 | 6.4 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxy-propylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula II

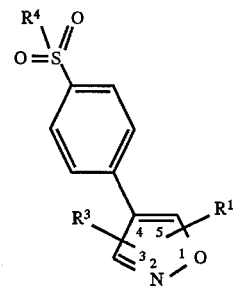

wherein $R^1$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl;

wherein $R^3$ is selected from cycloalkyl, cycloalkenyl, and aryl; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and wherein $R^4$ is selected from lower alkyl, hydroxyl, and amino;

or a pharmaceutically-acceptable salt thereof.

2. A compound of claim 1 wherein $R^1$ is selected from hydroxyl, amino, lower alkyl, lower carboxyalkyl, lower alkoxycarbonyl, aminocarbonyl, carboxyl, lower aminocarbonylalkyl, lower alkoxycarbonylalkyl, lower alkoxy, lower haloalkoxy, lower aralkoxy, lower cycloalkylalkoxy, lower alkylthio, lower aralkylthio, lower cycloalkylalkylthio, lower alkoxyalkyl, lower aralkoxyalkyl, lower alkylthioalkyl, lower aralkylthioalkyl, lower alkylaminoalkyl, lower aryloxyalkyl, lower arylthioalkyl, lower hydroxyalkyl, lower haloalkyl, lower cycloalkyl, lower cycloalkylalkyl, lower aralkyl, halo, lower alkylamino, lower aralkylamino, lower N-alkyl-N-aralkylamino, lower N-alkyl-N-cycloalkylalkylamino, lower arylcarbonyloxyalkyl, lower alkoxycarbonyloxyalkyl, lower alkylaminocarbonyloxyalkyl, lower alkoxycarbonylthioalkyl, and lower alkylaminocarbonylthioalkyl; wherein $R^3$ is selected from cycloalkyl, cycloalkenyl, and aryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, lower alkylsulfonyl, aminosulfonyl, and lower alkylthio; and wherein $R^4$ is selected from methyl, hydroxyl and amino; or a pharmaceutically-acceptable salt thereof.

3. A compound of claim 2 wherein $R^1$ is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxylalkyl, cycloalkyl, cycloalkylalkyl, and aralkyl; wherein $R^3$ is selected from cycloalkyl, cycloalkenyl, and aryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, aminosulfonyl, and lower alkylthio; and wherein $R^4$ is selected from methyl, hydroxyl and amino; or a pharmaceutically-acceptable salt thereof.

4. A compound of claim 3 wherein $R^1$ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzyloxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected form benzyl and phenylethyl, wherein the phenyl ring is optionally substituted at a substitutable position with fluoro, chloro, bromo, iodo, methyl, and methoxy; wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, and 1-cyclopentenyl; wherein $R^3$ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, nitro, fluoro, chloro, bromo, iodo, methoxy, ethoxy, propoxy, n-butoxy, pentoxy, hexyloxy, methylenedioxy, aminosulfonyl, methylthio, ethylthio, butylthio, and hexylthio; and wherein $R^4$ is selected from methyl, hydroxyl and amino; or a pharmaceutically-acceptable salt thereof.

5. The compound of claim 4 which is 4-[5-methyl-3-phenyl-isoxazol-4-yl]benzenesulfonamide, or a pharmaceutically-acceptable salt thereof.

6. A compound of Formula III

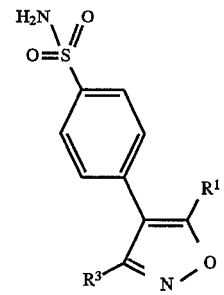

wherein $R^1$ is selected from hydroxyl, alkyl, carboxyalkyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl; and wherein $R^3$ is selected from cycloalkyl, cycloalkenyl, and aryl; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, aminosulfonyl, halo, alkoxy and alkylthio; or a pharmaceutically-acceptable salt thereof.

7. A compound of claim 6 wherein $R^1$ is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxylalkyl, lower cycloalkyl, lower cycloalkylalkyl, and aralkyl; wherein $R^3$ is selected from cycloalkyl, cycloalkenyl, and aryl; and wherein $R^3$ is optionally substituted at a substitutable position with one or more radicals independently selected from lower alkylsulfinyl, aminosulfonyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy and lower alkylthio; or a pharmaceutically-acceptable salt thereof.

8. A compound of claim 7 wherein $R^1$ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzyloxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected from phenylethyl and benzyl optionally substituted at a substitutable position with fluoro, chloro, bromo, iodo, methyl, and methoxy; and wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, and 1-cyclopentenyl; wherein $R^3$ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, aminomethyl, nitro, fluoro, chloro, bromo, iodo, methoxy, ethoxy, propoxy, n-butoxy, pentoxy, hexyloxy, methylenedioxy, methylthio, aminosulfonyl, ethylthio, butylthio, and hexylthio; or a pharmaceutically-acceptable salt thereof.

9. A pharmaceutical composition comprising a therapeutically-effective amount of a compound, said compound selected from a family of compounds of Formula II

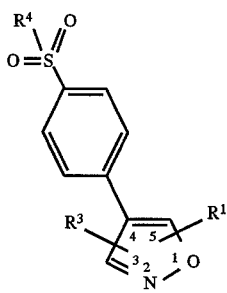

wherein $R^1$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl;

wherein $R^3$ is selected from cycloalkyl, cycloalkenyl, and aryl; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and wherein $R^4$ is selected from lower alkyl, hydroxyl, and amino;

or a pharmaceutically-acceptable salt thereof.

10. A pharmaceutical composition of claim 9 wherein $R^1$ is selected from hydroxyl, amino, lower alkyl, lower carboxyalkyl, lower alkoxycarbonyl, aminocarbonyl, carboxyl, lower aminocarbonylalkyl, lower alkoxycarbonylalkyl, lower alkoxy, lower haloalkoxy, lower aralkoxy, lower cycloalkylalkoxy, lower alkylthio, lower aralkylthio, lower cycloalkylalkylthio, lower alkoxyalkyl, lower aralkoxyalkyl, lower alkylthioalkyl, lower aralkylthioalkyl, lower alkylaminoalkyl, lower aryloxyalkyl, lower arylthioalkyl, lower hydroxyalkyl, lower haloalkyl, lower cycloalkyl, lower cycloalkylalkyl, lower aralkyl, halo, lower alkylamino, lower aralkylamino, lower N-alkyl-N-aralkylamino, lower N-alkyl-N-cycloalkylalkylamino, lower arylcarbonyloxyalkyl, lower alkoxycarbonyloxyalkyl, lower alkylaminocarbonyloxyalkyl, lower alkoxycarbonylthioalkyl, and lower alkylaminocarbonylthioalkyl; wherein $R^3$ is selected from cycloalkyl, cycloalkenyl, and aryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, lower alkylsulfonyl, aminosulfonyl, and lower alkylthio; and wherein $R^4$ is selected from methyl, hydroxyl and amino; or a pharmaceutically-acceptable salt thereof.

11. A pharmaceutical composition of claim 10 wherein $R^1$ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzyloxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, nitro, fluoro, chloro, bromo, iodo, methoxy, ethoxy, propoxy, n-butoxy, pentoxy, hexyloxy, methylenedioxy, aminosulfonyl, methylthio, ethylthio, butylthio, and hexylthio; and wherein $R^4$ is selected from methyl, hydroxyl and amino; or a pharmaceutically-acceptable salt thereof.

12. A pharmaceutical composition of claim 11 wherein said compound is 4-[5-methyl-3-phenyl-isoxazol-4-yl] benzenesulfonamide, or a pharmaceutically-acceptable salt thereof.

13. A pharmaceutical composition comprising a therapeutically-effective amount of a compound, said compound selected from a family of compounds of Formula III

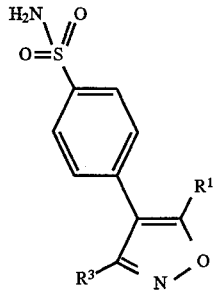

wherein R¹ is selected from hydroxyl, alkyl, carboxyalkyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl; and wherein R³ is selected from cycloalkyl, cycloalkenyl, and aryl; wherein R³ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, aminosulfonyl, halo, alkoxy and alkylthio; or a pharmaceutically-acceptable salt thereof.

14. A method of treating inflammation or an inflammation-associated disorder in a subject, said method comprising administering to the subject having or susceptible to said inflammation or inflammation-associated disorder, a therapeutically-effective amount of a compound of Formula II

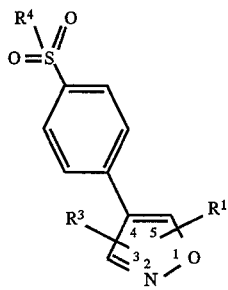

wherein R¹ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl;

wherein R³ is selected from cycloalkyl, cycloalkenyl, and aryl; wherein R³ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and wherein R⁴ is selected from lower alkyl, hydroxyl, and amino;

or a pharmaceutically-acceptable salt thereof.

15. A method of claim 14 wherein R¹ is selected from hydroxyl, amino, lower alkyl, lower carboxyalkyl, lower alkoxycarbonyl, aminocarbonyl, carboxyl, lower aminocarbonylalkyl, lower alkoxycarbonylalkyl, lower alkoxy, lower haloalkoxy, lower aralkoxy, lower cycloalkylalkoxy, lower alkylthio, lower aralkylthio, lower cycloalkylalkylthio, lower alkoxyalkyl, lower aralkoxyalkyl, lower alkylthioalkyl, lower aralkylthioalkyl, lower alkylaminoalkyl, lower aryloxyalkyl, lower arylthioalkyl, lower hydroxyalkyl, lower haloalkyl, lower cycloalkyl, lower cycloalkylalkyl, lower aralkyl, halo, lower alkylamino, lower aralkylamino, lower N-alkyl-N-aralkylamino, lower N-alkyl-N-cycloalkylalkylamino, lower arylcarbonyloxyalkyl, lower alkoxycarbonyloxyalkyl, lower alkylaminocarbonyloxyalkyl, lower alkoxycarbonylthioalkyl, and lower alkylaminocarbonylthioalkyl; wherein R³ is selected from cycloalkyl, cycloalkenyl, and aryl; wherein R³ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, lower alkylsulfonyl, aminosulfonyl, and lower alkylthio; and wherein R⁴ is selected from methyl, hydroxyl and amino; or a pharmaceutically-acceptable salt thereof.

16. A method of claim 15 wherein R¹ is selected from hydroxyl, methyl, ethyl, propyl, isopropyl, butyl, tert-butyl, isobutyl, pentyl, neopentyl, hexyl, carboxyl, carboxypropyl, carboxymethyl, carboxyethyl, benzyl, phenethyl, aminocarbonylmethyl, methoxycarbonylmethyl, methoxycarbonylethyl, methoxymethyl, benzyloxymethyl, phenylethoxymethyl, methylthiomethyl, benzylthiomethyl, N-methylaminomethyl, N,N-dimethylaminomethyl, phenyloxymethyl, phenylthiomethyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected form benzyl and phenylethyl, wherein the phenyl ring is optionally substituted at a substitutable position with fluoro, chloro, bromo, iodo, methyl, and methoxy; wherein R³ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, and 1-cyclopentenyl; wherein R³ is optionally substituted at a substitutable position with one or more radicals independently selected from trifluoromethoxy, N-methylamino, N,N-dimethylamino, N-ethylamino, N,N-dipropylamino, N-butylamino, N-methyl-N-ethylamino, phenylamino, N-methyl-N-phenylamino, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, amino, nitro, fluoro, chloro, bromo, iodo, methoxy, ethoxy, propoxy, n-butoxy, pentoxy, hexyloxy, methylenedioxy, aminosulfonyl, methylthio, ethylthio, butylthio, and hexylthio; and wherein $R^4$ is selected from methyl, hydroxyl and amino; or a pharmaceutically-acceptable salt thereof.

17. A method of claim 16 wherein said compound is 4-[5-methyl-3-phenyl-isoxazol-4-yl]benzenesulfonamide, or a pharmaceutically-acceptable salt thereof.

18. A method of treating inflammation or an inflammation-associated disorder in a subject, said method comprising administering to the subject having or susceptible to said inflammation or inflammation-associated disorder, a therapeutically-effective amount of a compound of Formula III

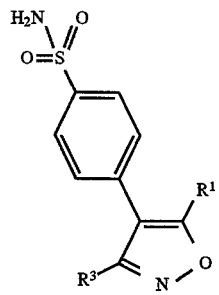

wherein $R^1$ is selected from hydroxyl, alkyl, carboxyalkyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl, and alkylaminocarbonylthioalkyl; and wherein $R^3$ is selected from cycloalkyl, cycloalkenyl, and aryl; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, aminosulfonyl, halo, alkoxy and alkylthio; or a pharmaceutically-acceptable salt thereof.

19. A method of claim 14 for use in treatment of inflammation.

20. A method of claim 14 for use in treatment of an inflammation-associated disorder.

21. A method of claim 20 wherein the inflammation-associated disorder is arthritis.

22. A method of claim 20 wherein the inflammation-associated disorder is pain.

23. A method of claim 20 wherein the inflammation-associated disorder is fever.

24. The compound of claim 4 selected from compounds, or their pharmaceutically acceptable salts, of the group consisting of 4-[5-ethyl-3-phenylisoxazol-4-yl]benzenesulfonamide;

4-[5-propyl-3-phenylisoxazol-4-yl]benzenesulfonamide;

4-[5-isopropyl-3-phenylisoxazol-4-yl] benzenesulfonamide;

4-[5-butyl-3-phenylisoxazol-4-yl]benzenesulfonamide;

4-[5-isobutyl-3-phenylisoxazol-4-yl] benzenesulfonamide;

4-[5-cyclohexyl-3-phenylisoxazol-4-yl] benzenesulfonamide;

4-[5-neopentyl-3-phenylisoxazol-4-yl] benzenesulfonamide;

4-[5-cyclohexylmethyl-3-phenylisoxazol-4-yl] benzenesulfonamide;

4-[5-(4-chlorophenyl)methyl-3-phenylisoxazol-4-yl] benzenesulfonamide;

4-[5-trifluoromethyl-3-phenylisoxazol-4-yl] benzenesulfonamide;

4-[5-difluoromethyl-3-phenylisoxazol-4-yl] benzenesulfonamide;

4-[5-chloromethyl-3-phenylisoxazol-4-yl] benzenesulfonamide;

4-[5-methyl-3-phenylisoxazol-4-yl]benzenesulfonic acid;

4-[5-propyl-3-phenylisoxazol-4-yl]benzenesulfonic acid;

4-[5-methoxymethyl-3-phenylisoxazol-4-yl] benzenesulfonamide;

4-[5-3-hydroxypropyl)-3-phenylisoxazol-4-yl] benzenesulfonamide;

4-[3-4-chlorophenyl)-5-methyl-isoxazol-4-yl] benzenesulfonamide;

4-[3-4-fluorophenyl)-5-methyl-isoxazol-4-yl] benzenesulfonamide;

4-[3-3-fluoro-4-methylphenyl)-5-methyl-isoxazol-4-yl] benzenesulfonamide;

4-[3-3-aminosulfonyl-4-methoxyphenyl)-5-methyl-isoxazol-4-yl]benzenesulfonamide;

4-[3-3-chloro-4-methylphenyl)-5-methyl-isoxazol-4-yl] benzenesulfonamide;

4-[3-3-fluorophenyl)-5-methyl-isoxazol-4-yl] benzenesulfonamide;

4-[5-hydroxymethyl-3-phenylisoxazol-4-yl] benzenesulfonamide;

[4-[4-(aminosulfonyl)phenyl]-3-phenylisoxazol-5-yl] carboxylic acid;

4-[5-hydroxy-3-phenyl-4-isoxazolyl] benzenesulfonamide;

4-[3-methyl-5-phenyl-isoxazol-4-yl] benzenesulfonamide;

4-[5-methyl-3-phenyl-isoxazol-4-yl] benzenesulfonamide;

4-[3-(3-fluoro-4-methoxyphenyl)-5-methyl-isoxazol-4-yl]benzenesulfonamide;

[3-(3-chloro-4-methoxyphenyl)-4-[4-(methylsulfonyl) phenyl]isoxazol-5-yl]acetic acid;

5-methyl-4-[4-(methylsulfonyl)phenyl]-3-phenyl-isoxazole;

3-(3-chloro-4-methoxyphenyl)-5-methyl-4-[4-(methylsulfonyl)phenyl]isoxazole;

[4-[4-(aminosulfonyl)phenyl]-3-phenyl-isoxazol-5-yl] acetic acid;

[4-[4-(aminosulfonyl)phenyl]-3-phenyl-isoxazol-5-yl] propanoic acid;

ethyl [4-[4-(aminosulfonyl)phenyl]-3-phenyl-isoxazol-5-yl]propanoate;

[3-(3-fluoro-4-methoxyphenyl)-4-[4-(methylsulfonyl) phenyl]isoxazol-5-yl]acetic acid; and

[4-[4-(aminosulfonyl)phenyl]-3-(3-fluoro-4-methoxyphenyl)isoxazol-5-yl]propanoic acid.

25. The compound of claim 4 which is 4-[5-hydroxymethyl-3-phenylisoxazol-4-yl]benzenesulfonamide, or a pharmaceutically-acceptable salt thereof.

26. A pharmaceutical composition of claim 11 wherein said compound is selected from compounds, or their pharmaceutically-acceptable salts, of the group consisting of 4-[5-ethyl-3-phenylisoxazol-4-yl]benzenesulfonamide;

4-[5-propyl-3-phenylisoxazol-4-yl]benzenesulfonamide;

4-[5-isopropyl-3-phenylisoxazol-4-yl] benzenesulfonamide;

4-[5-butyl-3-phenylisoxazol-4-yl]benzenesulfonamide;

4-[5-isobutyl-3-phenylisoxazol-4-yl] benzenesulfonamide;

4-[5-cyclohexyl-3-phenylisoxazol-4-yl] benzenesulfonamide;

4-[5-neopentyl-3-phenylisoxazol-4-yl] benzenesulfonamide;

4-[5-cyclohexylmethyl-3-phenylisoxazol-4-yl] benzenesulfonamide;

4-[5-(4-chlorophenyl)methyl-3-phenylisoxazol-4-yl] benzenesulfonamide;

4-[5-trifluoromethyl-3-phenylisoxazol-4-yl] benzenesulfonamide;

4-[5-difluoromethyl-3-phenylisoxazol-4-yl] benzenesulfonamide;

4-[5-chloromethyl-3-phenylisoxazol-4-yl] benzenesulfonamide;

4-[5-methyl-3-phenylisoxazol-4-yl]benzenesulfonic acid;

4-[5-propyl-3-phenylisoxazol-4-yl]benzenesulfonic acid;

4-[5-methoxymethyl-3-phenylisoxazol-4-yl] benzenesulfonamide;

4-[5-3-hydroxypropyl)-3-phenylisoxazol-4-yl] benzenesulfonamide;

4-[3-4-chlorophenyl)-5-methyl-isoxazol-4-yl] benzenesulfonamide;

4-[3-4-fluorophenyl)-5-methyl-isoxazol-4-yl] benzenesulfonamide;

4-[3-3-fluoro-4-methylphenyl)-5-methyl-isoxazol-4-yl] benzenesulfonamide;

4-[3-3-aminosulfonyl-4-methoxyphenyl)-5-methyl-isoxazol-4-yl]benzenesulfonamide;

4-[3-3-chloro-4-methylphenyl)-5-methyl-isoxazol-4-yl] benzenesulfonamide;

4-[3-3-fluorophenyl)-5-methyl-isoxazol-4-yl] benzenesulfonamide;

4-[5-hydroxymethyl-3-phenylisoxazol-4-yl] benzenesulfonamide;

[4-[4-(aminosulfonyl)phenyl]-3-phenylisoxazol-5-yl] carboxylic acid;

4-[5-hydroxy-3-phenyl-4-isoxazolyl] benzenesulfonamide;

4-[3-methyl-5-phenyl-isoxazol-4-yl] benzenesulfonamide;

4-[5-methyl-3-phenyl-isoxazol-4-yl] benzenesulfonamide;

4-[3-(3-fluoro-4-methoxyphenyl)-5-methyl-isoxazol-4-yl]benzenesulfonamide;

[3-(3-chloro-4-methoxyphenyl)-4-[4-(methylsulfonyl) phenyl]isoxazol-5-yl]acetic acid;

5-methyl-4-[4-(methylsulfonyl)phenyl]-3-phenyl-isoxazole;

3-(3-chloro-4-methoxyphenyl)-5-methyl-4-[4-(methylsulfonyl)phenyl]isoxazole;

[4-[4-(aminosulfonyl)phenyl]-3-phenyl-isoxazol-5-yl] acetic acid;

[4-[4-(aminosulfonyl)phenyl]-3-phenyl-isoxazol-5-yl] propanoic acid;

ethyl [4-[4-(aminosulfonyl)phenyl]-3-phenyl-isoxazol-5-yl]propanoate;

[3-(3-fluoro-4-methoxyphenyl)-4-[4-(methylsulfonyl) phenyl]isoxazol-5-yl]acetic acid; and

[4-[4-(aminosulfonyl)phenyl]-3-(3-fluoro-4-methoxyphenyl)isoxazol-5-yl]propanoic acid.

27. A pharmaceutical composition of claim 11 wherein said compound is 4-[5-hydroxymethyl-3-phenylisoxazol-4-yl]benzenesulfonamide, or a pharmaceutically-acceptable salt thereof.

28. A method of claim 16 wherein said compound is selected from compounds, or their pharmaceutically-acceptable salts, of the group consisting of 4-[5-ethyl-3-phenylisoxazol-4-yl]benzenesulfonamide;

4-[5-propyl-3-phenylisoxazol-4-yl]benzenesulfonamide;

4-[5isopropyl-3-phenylisoxazol-4-yl] benzenesulfonamide;

4-[5-butyl-3-phenylisoxazol-4-yl]benzenesulfonamide;

4-[5-isobutyl-3-phenylisoxazol-4-yl] benzenesulfonamide;

4-[5-cyclohexyl-3-phenylisoxazol-4-yl] benzenesulfonamide;

4-[5-neopentyl-3-phenylisoxazol-4-yl] benzenesulfonamide;

4-[5-cyclohexylmethyl-3-phenylisoxazol-4-yl] benzenesulfonamide;

4-[5-(4-chlorophenyl)methyl-3-phenylisoxazol-4-yl] benzenesulfonamide;

4-[5-trifluoromethyl-3-phenylisoxazol-4-yl] benzenesulfonamide;

4-[5-difluoromethyl-3-phenylisoxazol-4-yl] benzenesulfonamide;

4-[5-chloromethyl-3-phenylisoxazol-4-yl] benzenesulfonamide;

4-[5-methyl-3-phenylisoxazol-4-yl]benzenesulfonic acid;

4-[5-propyl-3-phenylisoxazol-4-yl]benzenesulfonic acid;

4-[5-methoxymethyl-3-phenylisoxazol-4-yl] benzenesulfonamide;

4-[5-(3-hydroxypropyl)-3-phenylisoxazol-4-yl] benzenesulfonamide;

4-[3-(4-chlorophenyl)-5-methyl-isoxazol-4-yl] benzenesulfonamide;

4-[3-(4-fluorophenyl)-5-methyl-isoxazol-4-yl] benzenesulfonamide;

4-[3-(3-fluoro-4-methylphenyl)-5-methyl-isoxazol-4-yl] benzenesulfonamide;

4-[3-(3-aminosulfonyl-4-methoxyphenyl)-5-methyl-isoxazol-4-yl]benzenesulfonamide;

4-[3-(3-chloro-4-methylphenyl)-5-methyl-isoxazol-4-yl]benzenesulfonamide;

4-[3-(3-fluorophenyl)-5-methyl-isoxazol-4-yl]benzenesulfonamide;

4-[5-hydroxymethyl-3-phenylisoxazol-4-yl]benzenesulfonamide;

[4-[4-(aminosulfonyl)phenyl]-3-phenylisoxazol-5-yl]carboxylic acid;

4-[5-hydroxy-3-phenyl-4-isoxazolyl]benzenesulfonamide;

4-[3-methyl-5-phenyl-isoxazol-4-yl]benzenesulfonamide;

4-[5-methyl-3-phenyl-isoxazol-4-yl]benzenesulfonamide;

4-[3-(3-fluoro-4-methoxyphenyl)-5-methyl-isoxazol-4-yl]benzenesulfonamide;

[3-(3-chloro-4-methoxyphenyl)-4-[4-(methylsulfonyl)phenyl]isoxazol-5-yl]acetic acid;

5-methyl-4-[4-(methylsulfonyl)phenyl]-3-phenyl-isoxazole;

3-(3-chloro-4-methoxyphenyl)-5-methyl-4-[4-(methylsulfonyl)phenyl]isoxazole;

[4-[4-(aminosulfonyl)phenyl]-3-phenyl-isoxazol-5-yl]acetic acid;

[4-[4-(aminosulfonyl)phenyl]-3-phenyl-isoxazol-5-yl]propanoic acid;

ethyl [4-[4-(aminosulfonyl)phenyl]-3-phenyl-isoxazol-5-yl]propanoate;

[3-(3-fluoro-4-methoxyphenyl)-4-[4-(methylsulfonyl)phenyl]isoxazol-5-yl]acetic acid; and

[4-[4-(aminosulfonyl)phenyl]-3-(3-fluoro-4-methoxyphenyl)isoxazol-5-yl]propanoic acid.

29. A method of claim 16 wherein said compound is 4-[5-hydroxymethyl-3-phenylisoxazol-4-yl]benzenesulfonamide, or a pharmaceutically-acceptable salt thereof.

* * * * *